(12) United States Patent
Zhou et al.

(10) Patent No.: US 8,101,158 B1
(45) Date of Patent: Jan. 24, 2012

(54) METHODS FOR TREATING CEREBROVASCULAR DISEASE COMPRISING ADMINISTERING AN AGENT THAT INHIBITS PROKINETICIN RECEPTOR ACTIVITY

(75) Inventors: Qun-Yong Zhou, Irvine, CA (US); Alex G. Lee, Palo Alto, CA (US); Michelle Y. Cheng, Monterey Park, CA (US); Robert M. Sapolsky, San Francisco, CA (US)

(73) Assignees: The Regents of the University of California, Oakland, CA (US); Stanford University, Stanford, CA (US)

( * ) Notice: Subject to any disclaimer, the term of this patent is extended or adjusted under 35 U.S.C. 154(b) by 229 days.

(21) Appl. No.: 12/025,673

(22) Filed: Feb. 4, 2008

Related U.S. Application Data

(60) Provisional application No. 60/899,112, filed on Feb. 2, 2007, provisional application No. 60/899,113, filed on Feb. 2, 2007.

(51) Int. Cl.
*A61K 49/00* (2006.01)
*A61K 31/535* (2006.01)
(52) U.S. Cl. ..................... 424/9.1; 514/231.2
(58) Field of Classification Search ............... None
See application file for complete search history.

(56) References Cited

U.S. PATENT DOCUMENTS
6,423,689 B1 * 7/2002 Booth et al. ............... 514/15.1

FOREIGN PATENT DOCUMENTS
| WO | WO2005/042717 | * | 5/2005 |
| WO | WO2007/067511 | * | 6/2007 |
| WO | WO2007067511 | * | 6/2007 |

OTHER PUBLICATIONS

Gorelick et al., JAMA, 281(12):1112-1120, 1999.*
Baram et al., "Neuropeptide-mediated Excitability: A Key Triggering Mechanism for Seizure Generation in the Developing Brain", *Trends Neuroscience*, vol. 21(11):471-476, 1998.
Cheng et al., "Prokineticin 2 Transmits the Behavioral Circadian Rhythm of the Suprachiasmatic Nucleus", *Nature*, vol. 417:405-410, 2002.
Cheng et al., "Regulation of Prokineticin 2 Expression by Light and the Circadian Clock", *BMC Neuroscience*, vol. 6(17), [electronic resource] 2005.
Cheng et al., "Expression of Prokineticins and their Receptors in the Adult Mouse Brain", *The Journal of Comparative Neurology*, vol. 498:796-809, 2006.
Cottrell et al., "Prokineticin 2 Modulates the Excitability of Subfornical Organ Neurons", *The Journal of Neuroscience*, vol. 24(10):2375-2379, 2004.
Lin et al., "Identification and Molecular Characterization of Two Closely Related G Protein-Coupled Receptors Activated by Prokineticins/Endocrine Gland Vascular Endothelial Growth Factor", *Journal of Biological Chemistry*, vol. 277(22):19276-19280, 2002.
Ng et al., "Dependence of Olfactory Bulb Neurogenesis on Prokineticin 2 Signaling", *Science* vol. 308:1923-1927 (includes supplementary information), 2005.
Zhou et al., Prokineticin 2 and Circadian Clock Output, *FEBS Journal*, vol. 272:5703-5709, 2005.

* cited by examiner

*Primary Examiner* — Lorraine Spector
*Assistant Examiner* — Stacey MacFarlane
(74) *Attorney, Agent, or Firm* — DLA Piper LLP (US)

(57) ABSTRACT

The present invention relates to a method of identifying agents that modulate prokineticin receptors, particularly, in the brain. Such agents are useful in the treatment of cerebrovascular diseases, including cerebral ischemia, cerebral hemorrhage, ischemic stroke, hemorrhagic stroke, and ischemic reperfusion injury. Additionally, such agents are useful to treat seizure disorders, such as epilepsy.

6 Claims, 12 Drawing Sheets

* p<0.05, ** p<0.01, n=4-7 / group

Compound I

A

B

A

B

C

METHODS FOR TREATING CEREBROVASCULAR DISEASE COMPRISING ADMINISTERING AN AGENT THAT INHIBITS PROKINETICIN RECEPTOR ACTIVITY

CROSS REFERENCE TO RELATED APPLICATION(S)

This application claims the benefit of priority under 35 U.S.C. §119(e) of U.S. Ser. No. 60/899,112, filed Feb. 2, 2007, and U.S. Ser. No. 60/899,113, filed Feb. 2, 2007, the entire contents of which are incorporated herein by reference.

GRANT INFORMATION

This invention was made with government support under grant MH067753 awarded by the National Institutes of Health. The government has certain rights in the invention.

BACKGROUND OF THE INVENTION

1. Field of the Invention

The present invention relates generally to a method for identifying agents effective in modulating prokineticin receptor, and more specifically to the treatment of cerebrovascular diseases and seizure disorders.

2. Background Information

Prokineticin receptors are G-protein coupled receptors that bind secreted proteins, namely, prokineticin 1 (PK1) and prokineticin 2 (PK2) inducing cellular responses. Prokineticins have roles in several biological functions, including circadian rhythm; angiogenesis; gastric contractility and motility; gastric acid and pepsinogen secretion; pain; and neurogenesis. The role of the prokineticin receptor pathway implicates improper prokineticin signaling in a variety of disease and disorders. As such, modulation of the prokineticin signaling pathway is implicated in treatment of a variety of disorders and diseases, such as such as cerebrovascular injury and seizure disorders. Accordingly, it is desirable to identify drugs that modulate receptor activity to treat associated disorders.

Cerebrovascular disease includes any abnormality of the brain resulting from a pathologic process of a blood vessel, including an occlusion of a blood vessel lumen by thrombus or embolus, a rupture of a blood vessel, an altered permeability of a blood-vessel wall, and increased viscosity or other change in the quality of blood. Cerebrovascular disease typically manifests as a stroke and characterized as the death of brain tissue that results from lack of blood flow and insufficient oxygen to the brain.

A stroke can be ischemic or hemorrhagic. In an ischemic stroke, the blood supply to part of the brain is reduced or terminated either by a blood clot that blocks a blood vessel or by atherosclerosis. Reducing or terminating blood flow to the brain is known as cerebral ischemia. Still cerebral ischemia can also arise from the failure of circulation and hypotension from severe and prolonged cardiac decompensation or shock. In a hemorrhagic stroke, the brain is damaged by a blood vessel bursting, which prevents normal blood flow and allows blood to leak into an area of the brain. When blood leaks into the brain, a hematoma is formed in the brain and blood can spread into ventricles and subarachnoid space. When cerebral ischemia is of sufficient severity and duration, cell injury can progress to cell death. When blood flow resumes to an organ after temporary cessation, this is known as ischemic reperfusion of the organ. Conditions observed with ischemia reperfusion injury include neutrophil infiltration, necrosis, and apoptosis.

Strokes are the leading cause of death in the United States after heart disease. Therefore, it is desirable to develop treatments for cerebrovascular diseases, including cerebral ischemia, cerebral hemorrhage, ischemic stroke, hemorrhagic stroke, and ischemic reperfusion injury.

Epilepsy is a prevalent neurological disorder, and an umbrella term that is used to describe multiple disorders of recurrent and unprovoked seizures. Genetic studies of human epilepsies and mouse mutants have indicated that voltage-gated ion channels are crucial elements in neuronal excitation and are therefore important in seizure initiation and propagation. Ligand-gated ion channels such as the $GABA_A$ receptor, glycine receptor and the nicotinic acetylcholine receptor have also been shown to mediate synaptic excitation and inhibition. Many anti-epileptic drugs (AED) used clinically act on these voltage-gated or ligand-gated ion channels to modify the bursting properties of neurons. However, it remains unclear how neural ensembles are synchronized and how abnormal discharge of neurons are propagated. Extracellular signaling molecules, including brain-derived neurotrophic factor (BDNF), thyrotropin-releasing hormone (TRH), corticotrophin releasing hormone (CRH) and neuropeptide Y (NPY), are upregulated as a result of seizure. These signaling molecules, in turn, may modulate neuronal membrane excitation and other neural plastic alterations important in epileptogenesis, such as gliosis, neuronal death and synaptic reorganization.

Accordingly, there exists a need to identify therapeutic agents useful in treating cerebrovascular disease and seizure disorders. The present invention satisfies this need, and provides related advantages as well.

SUMMARY OF THE INVENTION

The present invention relates to agents that inhibit or modulate prokineticin receptors and methods for identifying such agents.

In one embodiment, the present invention provides methods for identifying agents that reduce or prevent cerebrovascular disease. The method includes contacting a sample containing a PKR polypeptide with at least one test agent, and determining the ability of the test agent to inhibit prokineticin mRNA expression in a brain cell.

In another embodiment the present invention provides a method of identifying an agent that modulates epileptogenesis. The method includes contacting a sample containing a PKR polypeptide with at least one test agent, and determining the ability of the compound to modulate a GABA receptor signal.

In another embodiment, the present invention provides a method for preventing or treating a cerebrovascular disease or disorder in a subject. The method includes administering to the subject an agent that selectively binds to a prokineticin receptor and inhibits receptor activity, thereby treating cerebrovascular disease.

In another embodiment, the present invention provides a method for preventing or treating a seizure disorder in a subject. The method includes administering to the subject an agent that modulates PKR signaling, thereby preventing or treating the seizure disorder.

BRIEF DESCRIPTION OF THE DRAWINGS

FIG. 6A is a series of images showing post-ischemic increases in brain infarct size and volume comparing Compound I (antag) and control (PEG; polyethylene glycol 400) at different levels of the brain (from rostral to caudal, 1-6). FIG. 6B is a graphical representation showing a significant difference between Compound I (antagonist) and PEG (control) groups (*p<0.05, n=5) in infarct volume.

FIG. 7A shows a series of autoradiographic images depicting PK2 mRNA expression under basal conditions. FIG. 7B shows a series of autoradiographic images depicting PK2 mRNA expression 6 hours after pilocarpine-induced seizure. Pilocarpine-induced seizure caused dramatic induction of PK2 mRNA in various brain regions including the lateral septum (LS), dentate gyrus (DG), CA3 of hippocampus, central nucleus of amygdala (CeA), piriform cortex (Pir) as well as an ectopic expression of PK2 throughout the cortex. PK2 mRNA is also upregulated in a number of brain regions after pilocarpine-induced seizure, including the shell of nucleus accumbens (AcbSH), islands of Calleja (ICj), medial preoptic area (MPA), arcuate nucleus (Arc) and medial amygdala (Me). FIG. 7C shows an enlarged audioradiogram depicting PK2 mRNA expression 6 hours post seizure. FIG. 7D shows a dark field image depicting PK2 mRNA expression in the CeA after pilocarpine-induced seizure. White dotted lines outline the structure of lateral amygdala (LA), basolateral amygdala (BLA) and CeA.

FIG. 8A shows a series of audiogradiogram images demonstrating the temporal PK2 mRNA expression in mice brain slices after pilocarpine-induced seizure. FIG. 8B shows a series of graphical representations showing quantificational analysis of CeA, CA3 and dentate gyrus, after treatment with pilocarpine: from 0 hrs-72 hrs. PK2 induction within the CeA starts 30 minutes after injection of pilocarpine, gradually increases with respect to time, peaks at 6 hours, and gradually decreases to basal level by 72 hours. This trend, although not exactly, is similar for the CA3 and dentate gyrus as well. FIG. 8C shows a series of graphical representations showing inhibition of pilocarpine-induced seizure with Diazepam which blocks induction of PK2 in areas such as CeA, CA3 and dentate gyrus, suggesting that expression of PK2 is not due to pilocarpine but rather the seizure induced from pilocarpine.

FIG. 9A shows a series of audiogradiograms demonstrating the temporal PKR2 mRNA expression in mice brain slices after pilocarpine-induced seizure. FIG. 9B is a graphical representation showing quantificational analysis of CA1 and CA2 of the hippocampus, after treatment with pilocarpine: from 0 hrs-72 hrs.

FIG. 10A shows a dark field image depicting PK2 mRNA expression in the CeA after 6 hours post pilocarpine-induced seizure. PK2 mRNA induction in the CeA does not colocalize with corticotrophin releasing hormone (CRH). Black arrows indicate 35S-PK2 mRNA, white arrows indicate CRH mRNA expression. FIG. 10B shows a dark field image depicting PK2 mRNA expression in the CeA under basal conditions. PKR2 mRNA is colocalized with GABA in the amygdala, suggesting that PKR2 are present within the interneurons. FIG. 10C shows a dark field image depicting PK2 mRNA expression in the CeA after 6 hours post pilocarpine-induced seizure. PKR2 mRNA is colocalized with DAPI and PKR2 mRNA is colocalized with GABA and DAPI.

FIG. 11A shows a comparison of PK2 KO (N=11), and WT (N=15) mice with repeated injection of pilocarpine. Mice were given pilocarpine dose (200 mg/kg) every 30 minutes until S5 seizure was observed. KO mice required a significantly (student t-test p<0.01) less injection to reach S5 seizure. FIG. 11B shows a comparison of PK2 KO, and WT mice with single injection of high dose pilocarpine (400 mg/kg). All mice were observed behaviorally based on modified Racine scale (see methods) and some were co-monitored with electroencephalogram EEG. PK2 KO mice took significantly less time to reach S5 seizure, when compared to wild type control (N=13 p<0.05 unpaired student-t test). FIG. 11C shows an EEG depicting fast and continuous spikes >4 Hz. Red outline depicts onset time. All onset time were also confirmed with simultaneous behavioral observations.

FIG. 12A shows the percent of animals that reached kindling state on the given treatment day between WT and KO. FIG. 12B shows a comparison of kindling acquisition rate between KO and WT. Overall KO took significantly less time (N=11 student t-test p<0.05) to reach kindling state.

FIG. 13A shows GABA (10 uM) evoked GABA currents and addition of PK2 decreasing GABA evoked currents. GABA (10 uM) evoked GABA currents without PK2 show no appreciable reduction over a 70 min course. Addition of PK2 (10 nM-30 nM) decreased GABA-evoked current over a period of 60 min. FIG. 13B is a graphical representation showing the average percent reduction of normalized GABA-evoked currents after addition of PK2. The reduction of current is time dependent with a maximum inhibition of 75% of normalize baseline. One-way Anova with post-Dunnet correction indicates ($p<0.05$) across all time points when compared to normalized base.

DETAILED DESCRIPTION OF THE INVENTION

Figure 1:
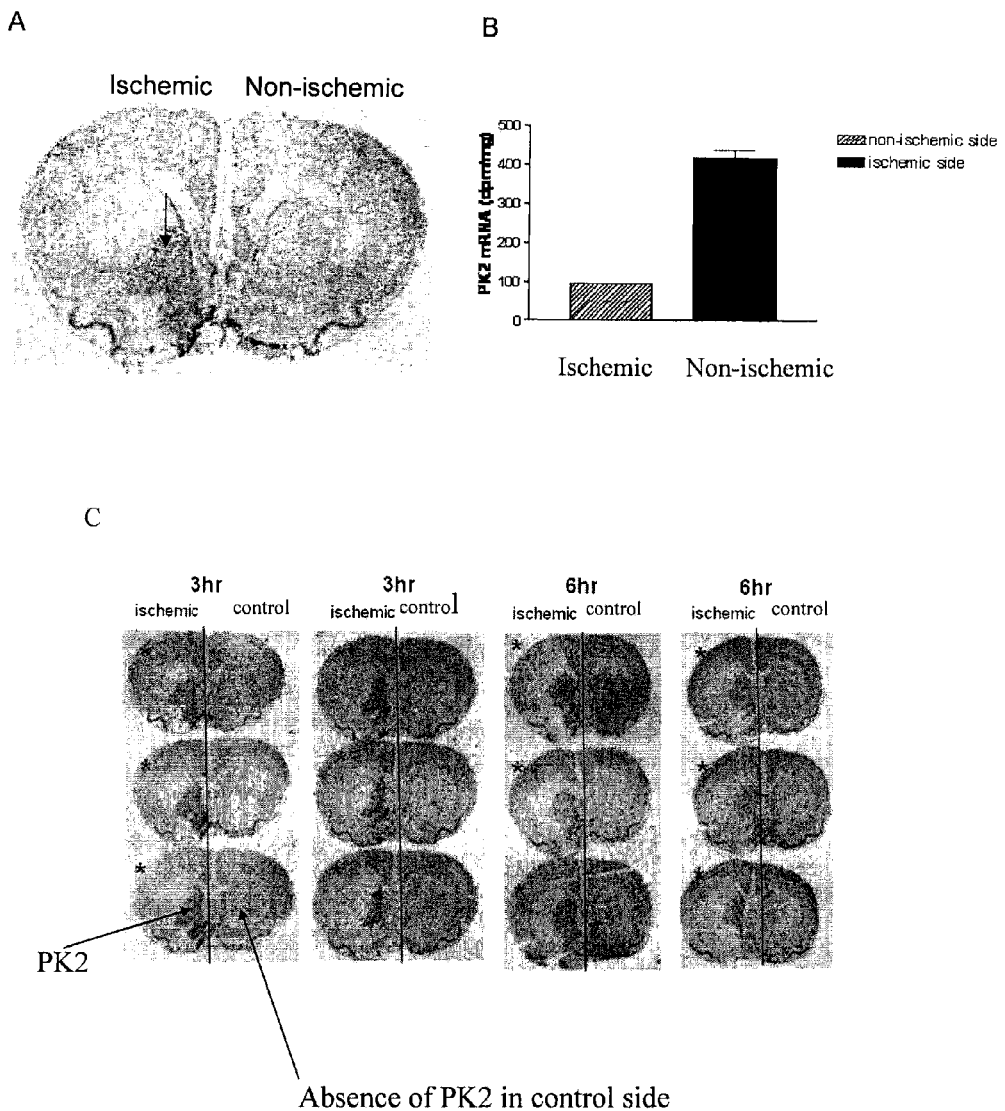
FIG. 1A is an image showing PK2 mRNA expression in the rat brain after an experimental stroke.
FIG. 1B is quantitation of PK2 mRNA expression 3 hours after MCAO in ischemic and non-ischemic side.
FIG. 1C is a series of images showing the time course of PK2 mRNA induction in the rat brain 3 and 6 hours after experimental stroke.

The present invention provides agents that inhibit or modulate prokineticin receptors and methods for identifying such agents. Additionally, the present invention provides methods of treating or preventing diseases or disorders associated with the PK/PKR signaling pathway, such as cerebrovascular disease and seizure disorders.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Prokineticin-2 (PK2) belongs to a family of newly identified secreted peptides that regulate diverse biological functions, including serving as a circadian output molecule and a chemoattractant for neuroprogenitor cells. The signaling of PK2 is mediated through two cognate G-protein coupled receptors (PKR1 and PKR2). PK2 is also known to modulate neuronal excitation, partially through modulation of inwardly rectifying K+ channels.

The present invention is based, in part, on the discovery that PKR agonists and antagonists, e.g., PK2, play a physiological role in seizure induction, including epileptogenesis, by modulation of the GABAergic system. Additionally, it has been discovered that PKR agonists and antagonists, e.g., PK2, play a physiological role in induction of cerebral ischemic injury and cerebrovascular disease.

Distribution analyses have revealed that PK2 and its receptors are expressed in a number of brain regions that are of importance in cerebrovascular diseases and epilepsy. For example, PK2 mRNA is expressed in the medial amygdale in addition to expression throughout the temporal and limbic regions, including the amygdaloid complex and the hippocampus. PK2 expression is also shown to be quickly and robustly induced by changes in neuronal activity, or under pathological conditions such as hypoxia.

As described herein, PK2 seizure is onset with pilocarpine and epileptogenesis as evidenced in a PTZ kindling model. After a pilocarpine-induced seizure, PK2 and its receptor (PKR2) mRNA are dramatically induced throughout the cortices, amygdala and hippocampus. Behavioral and EEG monitoring indicated that mice deficient in PK2 displayed lower latency time for seizures evoked with pilocarpine. PK2-deficient mice reached a faster kindling state after PTZ injection. In the amygdala, PKR2 receptor co-localized with $GABA_A$ receptor, suggesting an interaction between the GABA and the PK2 system. Using electrophysiological studies, exogenous PK2 attenuated $GABA_A$ receptor-evoked currents.

Accordingly, in one embodiment the present invention provides a method of identifying an agent that modulates epileptogenesis. The method includes contacting a sample containing a PKR polypeptide with at least one test agent, and determining the ability of the compound to modulate a GABA receptor signal.

The PK2 gene has multiple hypoxia responsive elements in its promoter. Accordingly, PK2 expression is inducible by hypoxia in vitro. It has been discovered that PK2 expression is induced post-ischemia. This implicates PK2 in ischemic injury. Additionally, it is shown that PK2 treated rats have larger infarct at almost every level, most prominent at the caudal level as shown herein.

Accordingly, in another embodiment, the present invention provides methods for identifying agents that reduce or prevent ischemic injury or cerebrovascular disease. The method includes contacting a sample containing a PKR polypeptide with at least one test agent, and determining the ability of the test agent to inhibit prokineticin mRNA expression in a brain cell. As used herein "brain cell" includes all cells derived from or included in brain tissue, such as neuronal and glial cells.

As used herein, the terms "sample" and "biological sample" refer to any sample suitable for the methods provided by the present invention. The sample can be any sample that may be used such that MBD protein activity can be detected. In one aspect, the sample is a biological sample, including, for example, a bodily fluid, an extract from a cell, which can be a crude extract or a fractionated extract, a chromosome, an organelle, or a cell membrane; a cell; genomic DNA, RNA, or cDNA, which can be in solution or bound to a solid support; a tissue; or a sample of an organ. A biological sample, for example, from a human subject, can be obtained using well known and routine clinical methods (e.g., a biopsy procedure).

An agent useful in any of the methods of the invention can be any type of molecule, for example, a polynucleotide, a peptide, a peptidomimetic, peptoids such as vinylogous peptoids, chemical compounds, such as organic molecules or small organic molecules, or the like, and can act in any of various ways to promote or diminish a PKR signal. For example, the agent may be an agonist or antagonist. Accordingly, in one aspect, an agent identified by the methods of the present invention is a chemical compound. In another aspect the compound is a morpholine carboxamide. In another aspect the compound is a pyrimidindione. In another aspect, the compound is Compound I. In yet another aspect, the compound is a muscarinic agent, such as methacholine and its chloride, carbachol, bethanechol, arecholine, pilocarpine, muscarine, McN-A-343, oxotremorine, milameline, xanomeline, cis-methyldioxalane, pirenzepine, gallamine, SB 202026, AF102B, AFDX 116 and RS-86.

Compounds of the invention can be modified and derivatized at multiple functional groups to enhance pharmacokinetic, pharmacodynamic, and biochemical properties. Such methods are commonly known to those of skill in the art.

In one aspect, the agent binds to a prokineticin receptor, thereby enhancing prokineticin binding to the prokineticin receptor or competing with prokineticin for the receptor. As such, the agent or compound can increase prokineticin receptor signal transduction, or can reduce or inhibit prokineticin signal transduction. In another aspect, the agent acts intracellularly to alter prokineticin signal transduction in the cell. In another aspect, the agent alters a specific interaction of prokineticin with a prokineticin receptor. Such an agent can be, for example, an agent that binds or otherwise sequesters prokineticin, thereby affecting the ability of prokineticin to interact specifically with its receptor.

The terms "agonism' and "antagonism" or equivalents thereof are well known in the art. The term "modulatory effect" or equivalents thereof, refers to the ability of the ligand, including an agonist or antagonist, to change the activity through binding to a ligand binding site. The term "ligand" as used herein, includes compounds that bind to the prokineticin receptor at the same or different site as prokineticin.

Although this invention is not limited to any particular theory, an "antagonist" or equivalents thereof, or an analogue of the antagonist according to the invention works to reduce or inhibit receptor activity and/or signaling. Such downregulation of receptor activity and/or signaling may be effectuated in a variety of ways, such as selective or non-selective binding to the PKR, or blocking binding of an agonist. An "agonist" or equivalents thereof, or an analogue of the agonist according to the invention works to promote or enhance PKR activity and/or signaling. Such upregulation of PKR activity and/or signaling may be effectuated in a variety of ways, such as selective or non-selective binding to the PKR.

As used herein, the term "modulate," when used in reference to an effect of an agonist or antagonist on a prokineticin receptor on a cell, means that prokineticin receptor signal transduction in the cell either is increased or is reduced or inhibited. The terms "increase" and "reduce" or "inhibit" are used in reference to a baseline level of prokineticin signal transduction activity, which can be the level of activity of the signal transduction pathway in the absence of prokineticin, or the level of activity in a normal cell in the presence of prokineticin. For example, the prokineticin signal transduction pathway exhibits a particular activity in a nerve cell contacted with the agent, such as an agonist or antagonist, and, upon further contacting the nerve cell with the agent or compound, or antagonist, prokineticin signal transduction activity can be reduced or inhibited. The terms and "reduce" or "inhibit" are used together herein because it is recognized that, in some cases, the level of prokineticin signal transduction can be reduced below a level that can be detected by a particular assay. As such, it may not be determinable using such an assay as to whether a low level of prokineticin signal transduction remains, or whether the signal transduction is completely inhibited.

The ability of a test agent to modulate an effect of prokineticin can be detected using methods as disclosed herein or otherwise known in the art. The term "test agent" or "test molecule" or "test compound" or equivalents thereof is used broadly herein to mean any agent or compound that is being examined for agonist or antagonist activity in a method of the invention. The term "test agent" is synonymous with "candidate compound". Although the method generally is used as a screening assay to identify previously unknown molecules that can act as agonist or antagonist agents as described herein, the methods also can be used to confirm that a agent known to have a particular activity in fact has the activity, for example, in standardizing the activity of the agent.

Test agents encompass numerous chemical classes, though typically they are chemical compounds, such as an organic molecule, and often are small organic compounds (i.e., small molecules) having a molecular weight of more than 100 Daltons and less than about 2,500 Daltons. Test agents comprise functional groups necessary for structural interaction with proteins, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs. If desired in a particular assay format, a candidate compound can be detectably labeled or attached to a solid support.

Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, Science 249:386-390, 1992; Markland et al., Gene 109:13 19, 1991; each of which is incorporated herein by reference); a peptide library (U.S. Pat. No. 5,264,563, which is incorporated herein by reference); a peptidomimetic library (Blondelle et al., Trends Anal. Chem. 14:83 92, 1995; a nucleic acid library (O'Connell et al., supra, 1996; Tuerk and Gold, supra, 1990; Gold et al., supra, 1995; each of which is incorporated herein by reference); an oligosaccharide library (York et al., Carb. Res., 285:99 128, 1996; Liang et al., Science, 274:1520 1522, 1996; Ding et al., Adv. Expt. Med. Biol., 376:261269, 1995; each of which is incorporated herein by reference); a lipoprotein library (de Kruif et al., FEBS Lett, 399:232 236, 1996, which is incorporated herein by reference); a glycoprotein or glycolipid library (Karaoglu et al., J. Cell Biol., 130:567 577, 1995, which is incorporated herein by reference); or a chemical library containing, for example, drugs or other pharmaceutical agents (Gordon et al., J. Med. Chem., 37:1385-1401, 1994; Ecker and Crooke, Bio/Technology, 13:351-360, 1995; each of which is incorporated herein by reference).

An agent useful in the methods of the invention also can be a polynucleotide. Polynucleotides can be particularly useful as agents that can modulate a specific interaction of prokineticin and its receptor because nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference).

A polynucleotide agent useful in a method of the invention can also be, or can encode, an antisense molecule, a ribozyme or a triplexing agent. For example, the polynucleotide can be (or can encode) an antisense nucleotide sequence such as an antisense c ski nucleotide sequence, which can increase prokineticin signal transduction in a cell; or an antisense nucleotide sequence, which can increase prokineticin signal transduction or can reduce or inhibit prokineticin signal transduction, depending on the particular antisense nucleotide sequence.

An antisense polynucleotide, ribozyme or triplexing agent is complementary to a target sequence, which can be a DNA or RNA sequence, for example, messenger RNA, and can be a coding sequence, a nucleotide sequence comprising an intron-exon junction, a regulatory sequence such as a Shine-Delgarno sequence, or the like. The degree of complementarity is such that the polynucleotide, for example, an antisense polynucleotide, can interact specifically with the target sequence in a cell. Depending on the total length of the antisense or other polynucleotide, one or a few mismatches with respect to the target sequence can be tolerated without losing the specificity of the polynucleotide for its target sequence. Thus, few if any mismatches would be tolerated in an antisense molecule consisting, for example, of 20 nucleotides, whereas several mismatches will not affect the hybridization efficiency of an antisense molecule that is complementary, for example, to the full length of a target mRNA encoding a cellular polypeptide. The number of mismatches that can be tolerated can be estimated, for example, using well known formulas for determining hybridization kinetics (see Sambrook et al., supra, 1989) or can be determined empirically using methods as disclosed herein or otherwise known in the art, particularly by determining that the presence of the antisense polynucleotide, ribozyme, or triplexing agent in a cell decreases the level of the target sequence or the expression of a polypeptide encoded by the target sequence in the cell.

A polynucleotide useful as an antisense molecule, a ribozyme or a triplexing agent can inhibit translation or cleave the nucleic acid molecule, thereby modulating prokineticin signal transduction in a cell. An antisense molecule, for example, can bind to an mRNA to form a double stranded molecule that cannot be translated in a cell. Antisense oligonucleotides of at least about 15 to 25 nucleotides are preferred since they are easily synthesized and can hybridize specifically with a target sequence, although longer antisense molecules can be expressed from a polynucleotide introduced into the target cell. Specific nucleotide sequences useful as antisense molecules can be identified using well known methods, for example, gene walking methods (see, for example, Seimiya et al., J. Biol. Chem. 272:4631-4636 (1997), which is incorporated herein by reference). Where the antisense molecule is contacted directly with a target cell, it can be operatively associated with a chemically reactive group such as iron-linked EDTA, which cleaves a target RNA at the site of hybridization. A triplexing agent, in comparison, can stall transcription (Maher et al., Antisense Res. Devel. 1:227 (1991); Helene, Anticancer Drug Design 6:569 (1991)). Thus, a triplexing agent can be designed to recognize, for example, a sequence of a Smad gene regulatory element, thereby reducing or inhibiting the expression of a Smad polypeptide in the cell, thereby modulating prokineticin signal transduction in a target cell.

As used herein, the term "prokineticin polypeptide" refers to a polypeptide comprising the amino acid sequence of a prokineticin 1 or prokineticin 2. As used herein, the term "prokineticin receptor polypeptide" refers to a polypeptide comprising the amino acid sequence of a prokineticin 1 or prokineticin 2 receptor. The polypeptides of the present invention may be derived from any source, including mammals, such as humans, non-human primates, mouse, rat, rabbit, bovine, porcine, ovine, canine or feline species, as well as sequences of their homologs in non-mammalian vertebrates, such as frogs and snakes. It is well known in the art that evolutionarily conserved amino acid residues and domains are more likely to be important for maintaining biological activity than less well-conserved residues and domains.

The polypeptides of the present invention may be isolated or membrane bound. As used herein, the term "isolated" indicates that the molecule is altered by the hand of man from how it is found in its natural environment. Preferably, an "isolated" prokineticin polypeptide can be a "substantially purified" molecule, that is at least 60%, 70%, 80%, 90 or 95% free from cellular components with which it is naturally associated. An isolated polypeptide can be in any form, such as in a buffered solution, a suspension, a lyophilized powder, recombinantly expressed in a heterologous cell, bound to a receptor or attached to a solid support.

"Defined-medium conditions" or equivalents thereof, e.g., "suitable conditions" refer to environments for culturing cells where the concentration of components therein required for optimal growth are detailed. For example, depending on the use of the cells (e.g., therapeutic applications), removing cells from conditions that contain xenogenic proteins is important; i.e., the culture conditions are animal-free conditions or free of non-human animal proteins.

The term "allosteric modulator" as used herein denotes a compound that can regulate the activity of a prokineticin receptor. The allosteric modulator can regulate the activity of a prokineticin receptor in several ways i.e., by increasing the affinity of a prokineticin receptor for its agonists and/or antagonists or decreasing the affinity of a prokineticin receptor for its agonists or antagonists. It can also regulate the prokineticin receptor's activity by effecting the association or dissociation of a prokineticin receptor agonist or antagonist.

The number of different test agents to test in the methods of the invention will depend on the application of the method. For example, one or a small number of candidate compounds can be advantageous in manual screening procedures, or when it is desired to compare efficacy among several predicted ligands, agonists or antagonists. However, it will be appreciated that the larger the number of candidate compounds, the greater the likelihood of identifying a compound having the desired activity in a screening assay.

A screening method of the invention provides the advantage that it can be adapted to high throughput analysis and, therefore, can be used to screen combinatorial libraries of test agents in order to identify those agents that can modulate an effect of prokineticin on a cell, including those agents that can alter a specific interaction of prokineticin and a prokineticin receptor.

A suitable preparation for a identifying a prokineticin receptor ligand can employ a tissue, cell, cell membrane, or purified prokineticin receptor. In one aspect the preparation employs a cell derived from brain tissue, such as a neuron or glial cell. In another aspect, the preparation employs a cell of the central nervous system. In another aspect, the preparation is a cell line that expresses prokineticin receptor, or membrane preparation thereof. A cell line that expresses prokineticin receptor can be identified by methods known in the art, such as the competitive binding assays.

A suitable control cell line that does not express prokineticin receptor is HEK293 (available from American Type Culture Collection as CRL-1573). Other control cell include COS-7, COS-1, Ltk-, NIH3T3, C6,NS10Y and HT-29 cells.

Appropriate assays to identify receptor ligands are known in the art. Such assays can involve directly determining binding of the candidate compound to the receptor preparation. Direct assays are suitable when an appropriate control preparation is available that does not contain the prokineticin receptor. Such assays can also involve determining the ability of the test agent to compete with a prokineticin polypeptide for binding to the receptor preparation. Competition assays can be performed by detectably labeling a candidate compound and competing the compound with an unlabeled prokineticin polypeptide, or competing an unlabeled candidate compound with a detectably labeled prokineticin polypeptide.

Various detectable labels are provided herein, for example, radiolabels linked to the various components or building blocks (e.g., acetate, tetrose, and non-proteinogenic amino acid) or even antibodies against the described building blocks, using various chemical linking groups or bifunctional peptide linkers. A terminal hydroxyl can be esterified with inorganic acids, e.g., $^{32}P$ phosphate, or $^{14}C$ organic acids, or else esterified to provide linking groups to the label. Enzymes of interest as detectable labels will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol), and the like.

Antibodies are provided which bind to any of the biosynthetic components of salinosporamide A and/or its analog thereof. These antibodies may also be attached to solid supports, e.g., antibodies are particularly useful for immunoassays or immunoprecipitation of any of the polypeptide. Such solid supports include, but are not limited to, glass, cellulose, polyacrylamide, nylon, polystyrene, polyvinyl chloride or polypropylene, for example protein G covered wells of microtiter plates or beads.

Antibodies directed against a specific epitope, or combination of epitopes, so as to bind specifically with any of the biosynthetic components of salinosporamide A and/or its analog thereof will allow for the screening of, for example, cell populations as described herein. Various screening techniques can be utilized using such polyclonal and monoclonal antibodies, and including magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

The antibodies useful in the invention methods may be assayed for immunospecific binding by any method known in the art. The immunoassays which can be used, include but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., Western blot analysis. Those of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or 125I) diluted in blocking buffer, washing the membrane in wash buffer, and detecting the presence of the antigen. Those of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. Those of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays.

In this case, the antigen is incubated with the antibody of interest conjugated to a labeled compound (e.g., $^3$H or $^{125}$I) in the presence of increasing amounts of an unlabeled second antibody.

Antibodies used in invention assay(s) can be polyclonal, monoclonal, or a functionally active fragment thereof. Mono- or poly-clonal antibodies to a salinosporamide A are raised in appropriate host animals by immunization with immunogenic conjugate(s) using conventional techniques as are known in the art.

The preparation of monoclonal antibodies is disclosed, for example, by Kohler and Milstein, Nature 256:495-7, 1975; and Harlow et al., in: Antibodies: a Laboratory Manual, page 726 (Cold Spring Harbor Pub., 1988), which are hereby incorporated by reference. Briefly, monoclonal antibodies can be obtained by injecting mice, or other small mammals, such as rabbits, with a composition comprising an invention immunogenic conjugate whose preparation is disclosed above, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Barnes et al., Purification of Immunoglobulin G (IgG), in: Methods in Mol. Biol., 10: 79-104,1992). Antibodies of the present invention may also be derived from subhuman primate antibodies. General techniques for raising antibodies in baboons can be found, for example, in Goldenberg et al., International Patent Publication WO 91/11465 (1991) and Losman et al., Int. J. Cancer, 46:310-314, 1990.

It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The term "antibody" as used in this invention includes intact molecules as well as functional fragments thereof, such as Fab, F(ab')$_2$, and Fv that are capable of binding salinosporamide A polypeptide These functional antibody fragments are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

Antibody fragments according to the present invention can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Hybridoma cell lines producing monoclonal antibodies useful in the invention methods for immunocapture of any biosynthetic component(s) of the salinosporamide A or B and their analogs thereof can be made or are commercially available.

Suitable receptor binding assays, including high-throughput assays, are described, for example, in Mellentin-Micelotti et al., Anal. Biochem. 272: P182-190 (1999); Zuck et al., Proc. Natl. Acad. Sci. USA 96: 11122-11127 (1999); and Zhang et al., Anal. Biochem. 268; 134-142 (1999). Other suitable assays for detecting binding include, for example, scintillation proximity assays (SPA) (Alouani, Methods Mol. Biol. 138: 135-41 (2000)), UV or chemical cross-linking (Fancy, Curr. Opin. Chem. Biol. 4: 28-33 (2000)), competition binding assays (Yamamura et al., Methods in Neurotransmitter Receptor Analysis, RavenPress, New York, 1990), biomolecular interaction analysis (BIA) such as surface plasmon resonance (SPR) (Weinberger et al., Pharmacogenomics 1: 395-416 (2000)), mass spectrometry (MS) (McLafferty et al., Science 284: 12891290 (1999) and Degterev, et al., Nature Cell Biology 3: 173-182 (2001)), nuclear magnetic resonance (NMR) (Shuker et al., Science 274: 1531-1534 (1996), Hajduk et al., J. Med. Chem. 42: 2315-2317 (1999), and Chen and Shapiro, Anal. Chem. 71: 669A-675A (1999)), and fluorescence polarization assays (FPA) (Degterev et al., supra, 2001).

An appropriate binding assay can be chosen depending the nature and purity of the receptor preparation and the number and nature of the test agents.

A screening method of the invention can be performed, for example, by contacting under suitable conditions an agonist or antagonist, or a functional peptide portion thereof, to a prokineticin receptor. For example, PK1 or PK2 or a functional fragment thereof can be contacted to a PKR1 or PKR2. The prokineticin, the prokineticin receptor and the agent can be contacted in any order as desired. As such, the screening method can be used to identify agents that can competitively or non competitively inhibit prokineticin binding to the receptor, agents that can mediate or enhance prokineticin binding to the receptor, agents that can induce dissociation of specifically bound prokineticin from the receptor, and agents that otherwise affect the ability of prokineticin to induce signal transduction, such agents having agonist or antagonist activity. Appropriate control reactions are performed to confirm that the action of the agent is specific with respect to the prokineticin receptor, functional fragments thereof, or other prokineticin receptors.

Suitable conditions or defined conditions for performing a screening method of the invention can be any conditions that allow prokineticin to specifically interact with its receptor, including methods as disclosed herein or otherwise known in the art. Thus, suitable conditions for performing the screening assay can be, for example, in vitro conditions using a substantially purified prokineticin receptor; cell culture conditions, utilizing a cell that normally expresses a prokineticin receptor, for example, a neuron or glia cell, or a cell that has been genetically modified to express a functional prokineticin receptor on its surface; or in situ conditions as occur in an organism.

A screening method of the invention also can be performed using the methods of molecular modelling as described above. The utilization of a molecular modelling method provides a convenient, cost effective means to identify those agents, among a large population such as a combinatorial library of potential agents that are most likely to interact specifically with a prokineticin receptor, thereby reducing the number of potential agents that need to be screened using a biological assay. Upon identifying agents that interact specifically with a prokineticin receptor such as prokineticin using a molecular modelling method, the selected agents can be examined for the ability to modulate an effect of an agent, such as prokineticin, on a cell using the methods disclosed herein.

An expression vector (or the polynucleotide) generally contains or encodes a promoter sequence, which can provide constitutive or, if desired, inducible or tissue specific or developmental stage specific expression of the encoding polynucleotide, a poly A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb. 25:37 42, 1993; Kirshenbaum et al., J. Clin. Invest. 92:381-387, 1993; each of which is incorporated herein by reference).

A tetracycline (tet) inducible promoter can be particularly useful for driving expression of a polynucleotide of the invention, for example, a polynucleotide encoding a prokineticin and prokineticin receptors or functional fragments thereof, which have prokineticin activity or having receptor binding activity. Upon administration of tetracycline, or a tetracycline analog, to a subject containing a polynucleotide operatively linked to a tet inducible promoter, expression of the encoded peptide is induced, whereby the peptide can effect its activity, for example, whereby a peptide agent can reduce or inhibit prokineticin signal transduction. Such a method can be used, for example, to induce seizures in a mammalian organism.

The polynucleotide also can be operatively linked to tissue specific regulatory element, for example, a neural or glia cell specific regulatory element, such that expression of an encoded peptide is restricted to neurons and/or glia cells in an individual, or to neurons and/or glia cells in a mixed population of cells in culture, for example, an organ culture.

A polynucleotide, which can be contained in a vector, can be introduced into a cell by any of a variety of methods known in the art (Sambrook et al., Molecular Cloning: A laboratory manual (Cold Spring Harbor Laboratory Press 1989); Ausubel et al., Current Protocols in Molecular Biology, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Assay methods for identifying compounds that selectively bind to or modulate signaling through a prokineticin receptor (e.g. ligands, agonists and antagonists) generally involve comparison to a control.

One type of a "control" is a preparation that is treated identically to the test preparation, except the control is not exposed to the test compound. Another type of "control" is a preparation that is similar to the test preparation, except that the control preparation does not express the receptor, or has been modified so as not to respond selectively to prokineticin. In this situation, the response of the test preparation to a candidate compound is compared to the response (or lack of response) of the control preparation to the same compound under substantially the same reaction conditions.

A compound that is determined to be a prokineticin receptor ligand can further be tested to determine whether it is an agonist or antagonist of prokineticin receptor. Likewise, a compound that is determined to be a prokineticin receptor ligand can further be tested to determine whether it modulates, either positively or negatively, cerebral ischemia or seizures, using an in vitro or in vivo assay, such as the assays described herein.

The invention methods can be performed in the presence of a suitable concentration of a prokineticin, such as within 10-fold of its EC, 50. Thus, an agonist that competes with prokineticin for signaling through the prokineticin receptor, or indirectly potentiates the signaling activity of prokineticin, can be readily identified. Likewise, an antagonist that prevents prokineticin from binding the prokineticin receptor, or indirectly decreases the signaling activity of prokineticin, can also be identified.

In one embodiment, the present invention provides a method for preventing or treating a seizure disorder in a subject. The method includes administering to the subject an agent that modulates PKR signaling, thereby preventing or treating the seizure disorder. In one aspect, the agent is an agonist and acts to increase PKR signaling.

As used herein, seizure disorder includes all disorders associated with seizures, such as epilepsy. Such seizures and seizure disorders include, for example, simple partial seizures Jacksonian seizures, complex partial (psychomotor) seizures, epilepsia partialis continua, tonic-clonic (grand mal) seizures, primary generalized epilepsy, absence (petit mal) seizures, atonic seizures, myoclonic seizures, and status epilepticus.

In another embodiment, the present invention provides a method for preventing or treating a cerebrovascular disease or disorder in a subject. The method includes administering to the subject an agent that selectively binds to a prokineticin receptor and inhibits receptor activity, thereby treating cerebrovascular disease. In one aspect, the agent is Compound I.

As used herein, cerebrovascular diseases, include cerebral ischemia, cerebral hemorrhage, ischemic stroke, hemorrhagic stroke, and ischemia reperfusion injury resulting from reintroduction of blood flow following cerebral ischemia or ischemic stroke.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, the term "ameliorating" or "treating" means that the clinical signs and/or the symptoms associated with the cancer or disease, such as sickle cell anemia, are lessened as a result of the actions performed. The signs or symptoms to be monitored will be characteristic of the particular disease and will be well known to the skilled clinician, as will the methods for monitoring the signs and conditions. For example, the skilled clinician will know that the magnitude or duration of seizure can be monitored.

A "therapeutically effective amount" as used herein includes a prophylactic amount, for example, an amount effective for preventing or protecting against cerebrovascular disease or symptoms thereof and amounts effective for alleviating or healing cerebrovascular disease or symptoms thereof and preventing or treating seizure disorders, such as epilepsy. For therapeutic applications, a prokineticin receptor agonist preferably has an $EC_{50}$, and a prokineticin receptor antagonist preferably has an $IC_{50}$, of less than about 10"M, such as less than 10-8M, and more preferably less than 10-9 or 10-1 M. However, depending on the stability, selectivity and toxicity of the compound, a prokineticin receptor agonist with a higher $EC_{50}$, or a prokineticin receptor antagonist with a higher $IC_{50}$, can also be useful therapeutically.

Alternatively, an appropriate amount and formulation for a particular therapeutic application in humans can be extrapolated based on the activity of the compound in the in vitro binding and signaling assays described herein, or from recognized animal models of the particular disorder.

For example, a therapeutically effective amount includes an amount suitable for preventing or protecting against cerebral ischemia, cerebral hemorrhage, ischemic stroke, hemorrhagic stroke, or ischemic reperfusion injury resulting from reintroduction of blood flow following ischemic stroke or cerebral ischemia. Moreover, a therapeutically effective amount includes an amount suitable for alleviating or healing cerebral ischemia, cerebral hemorrhage, ischemic stroke, hemorrhagic stroke, or ischemic reperfusion injury resulting from reintroduction of blood flow following ischemic stroke or cerebral ischemia.

A therapeutic agent can be administered prior to ischemia to prevent, inhibit, or protect against ischemia reperfusion injury to the brain. In an alternative aspect, a composition of the invention can be administered during or following ischemia (including during or following reperfusion) to alleviate or heal ischemia reperfusion injury of the brain. Additionally, therapeutic agents can be administered prior to a seizure to prevent, inhibit, or protect against onset of the seizure.

The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The agent can be administered in any way typical of an agent used to treat the particular disorder or disease, or under conditions that facilitate contact of the agent with the target cells or tissues and, if appropriate, entry into the cells. Entry of a polynucleotide agent into a cell, for example, can be facilitated by incorporating the polynucleotide into a viral vector that can infect the cells. If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell. Generally, an agent is formulated in a composition (e.g., a pharmaceutical composition) suitable for administration to the subject.

The total amount of therapeutic agent can be administered as a single dose or by infusion over a relatively short period of time, or can be administered in multiple doses administered over a more prolonged period of time. Additionally, the agent can be administered in a slow-release matrix, which can be implanted for systemic delivery at or near the site of the target tissue.

For applications that require the agents and compositions to cross the blood-brain barrier, or to cross cell membranes, formulations that increase the lipophilicity of the compound are particularly desirable.

For example, the agent of the invention can be incorporated into liposomes (Gregoriadis, Liposome Technology, Vols. I to III, 2nd ed. (CRC Press, BocaRaton Fla. (1993)). Liposomes, which consist of phospholipids or other lipids, are nontoxic, physiologically acceptable and metabolizable carriers that are relatively simple to make and administer.

The present invention is more particularly described in the following examples which are intended as illustrative only since numerous modifications and variations therein will be apparent to those skilled in the art.

Example I

Methods for the Infusion, Stroke Model, Staining and Quantitation

Distal Middle Cerebral Artery Occlusion (dMCAO) was performed in the PK2 intracerebroventricular (ICY) infusion study. Anesthesia induced by 5% isoflurane and maintained by 2-3% isoflurane. A ventral midline incision was made, and the two CCAs were isolated. Snares were placed around the CCAs, and the animal was placed on its right side. A 2-cm vertical scalp incision was made midway between the left eye and ear. The temporalis muscle was bisected and a 2-mm burr hole was made at the junction of the zygomatic arch and squamous bone to expose the distal MCA. The dura was cut and the distal MCA was permanently electro-cauterized. The CCA were then occluded with clips for 1 hour, and the animals were sacrificed and perfused after 24 hr.

PK2 (0.3 nmol) was stereotaxically infused prior or post-ischemia. Animals were anesthetized starting with 5% isoflurane, then maintained on 2-3% isoflurane. Body temperature, ECG, and respiration rate were monitored every 15 minutes and kept in physiological ranges. Rats were anchored in a stereotaxic station and the skin on top of the head was opened. A small hole was exposed with a drill without damaging the tissue. A 10 ul hamilton syringe needle was stereotaxically inserted into the lateral ventricle (From Bregma, AP=−0.92 mm, ML=1.5 mm, DV=3.5 mm), and PK2 or SAL was infused with a microinfusion pump at 1 ul/min.

TTC staining and infarct quantification was performed as follows. 24 hours after reperfusion, rats were perfused with ice cold PBS and the brain was sectioned into 2 mm thickness. Brain sections were stained with 2,3,5 triphenyl tetrazolium chloride (TTC) solution for 15 minutes or until infarct was visible, followed by fixation with 4% PFA overnight. Next day the brain sections were aligned from rostral to caudal and brain sections were scanned. Infarct size and volume was quantitated using the software Image J. Infarct and cortex was outlined and measured using Image J. Percent infarct represents infarct area over entire cortex area. Percent volume was measured by multiplying the area by the section thickness (2 mm).

Example II

Methods for PK2 Induction and the Stroke Model Used

Intraluminal Middle Cerebral Artery Occlusion (MCAO) was performed as follows. Male Sprague Dawley rats (280-320 g) were used. Animals were anesthetized starting with 5% isoflurane, then maintained on 2-3% isoflurane. Body temperature, ECG, and respiration rate were monitored every 15 minutes and kept in physiological ranges. MCAO was be performed using an intraluminal suture (1 hr occlusion), and rats were sacrificed 24 hr after reperfusion. For MCAO, the common carotid, external carotid, and pterygopalatine arteries were exposed and ligated on the left side. The left internal carotid artery was transiently occluded with a microsurgical clip, and an arteriotomy was made in the common carotid artery. A 3.0-monofilament suture with a rounded tip will be inserted into the common carotid artery and advanced through the internal carotid artery to the ostium of the middle cerebral artery (MCA) to occlude the MCA. Rats were sacrificed at 3 hr after MCAO and processed for in situ hybridization.

In situ hybridization was performed as follows. For mRNA analysis, brains were quickly removed and frozen in −20□C isopentane. Brains were sectioned and in situ hybridization was carried out as described previously. Briefly, sections were pretreated with proteinase K (1 ug/ml), acetylated, dehydrated, and air dried. Sections were hybridized with PK2 riboprobe (accession number AF487280) and incubated at 60° C. for 18 hours, followed by RNAase digestion, decreasing salinity washes, and a 30-minute high-stringency (68° C.) wash. After dehydration and air drying, tissue sections were exposed to Kodak Biomax film for 3 days. Autoradiograms were developed and analyzed using the MCID image analysis system.

Example III

PK2 MRNA Expression is Increased in Cerebral Ischemia

The PK2 gene has multiple hypoxia responsive elements in its promoter.

Previous study showed that PK2 expression is inducible by hypoxia in vitro. To investigate the role of PK2 in cerebral ischemia, whether PK2 expression is inducible in experimental stroke models was first examined. A middle cerebral artery occlusion (MCAO) using an intraluminal suture that produces infarct in the striatum and/or cortex was performed. FIG. 1A is a representative autoradiographic image of PK2 mRNA induction in the brain after experimental stroke. FIG. 1B is quantitation of PK2 mRNA expression 3 hours after MCAO in ischemic and non-ischemic side. Three hours after reperfusion, rats were sacrificed and processed for in situ hybridization to examine PK2 mRNA expression. n=3, ***p<0.001. PK2 mRNA expression is induced in the striatum on the ischemic side.

FIG. 1C shows time course of PK2 mRNA induction in the brain 3 and 6 hr after experimental stroke. It is apparent that PK2 mRNA induction was only present in the ischemic side, but absent in the non-ischemic side. Also samples of 3 hr showed relatively stronger signal than that of 6 hr. A distal MCAO model that produces infarct only in cortex was also used to examine PK2 induction. Similar to intraluminal MCAO, distal MCAO model also induces PK2 in the striatum. Interestingly, PK2 induction in the striatum is only detected in peri-infarct regions.

Example IV

Exogenous Delivery of PK2 Increases Infarct Size

PK2 expression is induced post-ischemia indicating a potential role for PK2 in ischemic injury. The effect of exogenous delivery of PK2 on infarct volume was tested. FIG. 2A are images depicting representative ITC stained rat brains that had experimental stroke. Distal MCAO that produces infarct in cortex were used in this study, as this model produces more consistent infarct size. Animals underwent distal MCAO for 30 minutes. Within one hour after reperfusion, PK2 (0.3 nmol) or saline (SAL) was infused stereotaxically into the lateral ventricle on the ischemic side. Animals were sacrificed after 24 hr, followed by TTC staining to examine infarct size. White areas represent infarct tissue. Brain sections (2 mm thickness) are aligned from rostral to caudal to show the extent of infarct. PK2-treated rats have larger infarct size than saline (SAL) treated rats. FIGS. 2B and C are graphs showing quantitation of infarct volume. FIG. 2B shows the difference between SAL and PK2 group at different levels of the brain (from rostral to caudal). PK2 treated rats have larger infarct at almost every level, most prominent at the caudal level. Two-way ANOVA with bonferroni's posthoc statistical analysis showed that there is a significant difference between PK2 and SAL groups at level 6. FIG. 2C shows the same data as shown in FIG. 2B, but plotted as a mean result from all 6 levels. Two-way ANOVA analysis indicates that PK2 significantly increased overall average infarct volume. ***$p<0.001$. n=5. The dose of PK2 (0.3 nmol) was based on previous studies that used in running wheel experiments. This dose elicits an inhibitory response in locomotor running wheel activity that lasts for 3-5 hours. FIG. 2D shows the dose dependent effect of PK2 on increasing average infarct volume.

Example V

PKR2 Antagonists that Reduce Infarct Size

To date potent peptide-based PK2 antagonists with $K_i$ values of about 50 nM have been developed. Recently, pharmaceutical companies have developed selective and more potent small molecule PKR2 antagonists, such as morpholine carboxamide prokineticin receptor antagonists and pyrimidindione derivatives. The $K_i$ values of these antagonists in blocking PKR2 receptor activation in vitro are 10 nM or smaller. Whereas the brain penetrance of pyrimidindione derivatives is unclear, the morpholine carboxamide family of PKR2 antagonist possesses significant ability to cross blood brain barrier.

Figure 4:
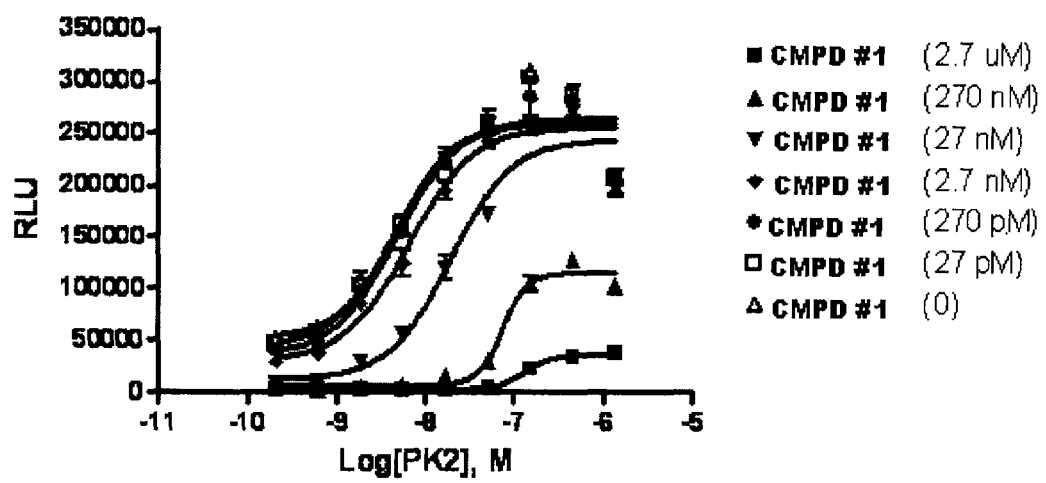
FIG. 4 is a graphical representation showing the antagonistic effect of Compound I in Chinese Hamster Ovary cells that stably express PKR2. Dose-dependent response of PKR2 activation by PK2 in the presence of different concentrations of Compound I was measured with a luminometer. RLU is an index for calcium influx measurement for this luminescence-based assay. The dose-dependent calcium influx activated by PK2 was antagonized by Compound I. The inhibition constant obtained from this experiment was approximately 15 nM.
Figure 5:
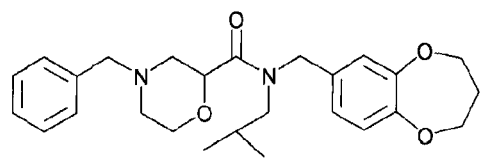
FIG. 5 is a pictorial representation of Compound I.

Via custom synthesis, 10 grams of one of the morpholine carboximide derivatives was obtained, with chemical name of (±)-4-Benzyl-N-(3,4-dihydro-2H-1,5-benzodioxepin-7-yl-methyl)-N-isobutylmorpholine-2-carboxamide, compound I (FIG. 5). Compound I was tested using the in vitro ischemia model. The in vitro testing has indicated that compound I blocks the activation of PKR2 in Chinese Hamster Ovary cells in a dose-dependent manner, with $K_i$ values of about 15 nM (FIG. 4). Pharmacokinetic study has revealed significant brain concentration of compound I, following intraperitoneal injection of 60 mg/kg in rats. We utilized compound I as a parent compound to test the potential therapeutic effect of blocking PKR2 in cerebral ischemia models.

Figure 6:
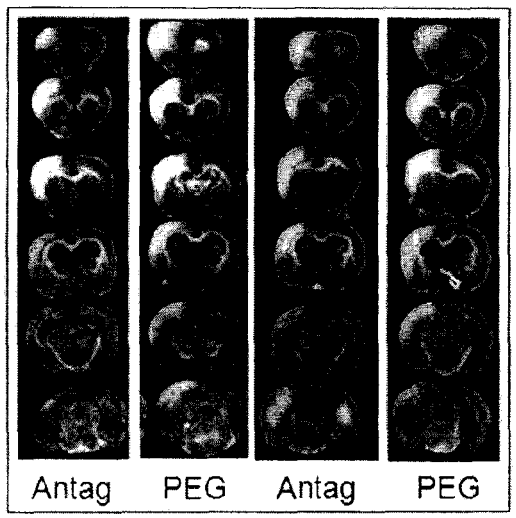
FIGS. 6A-B show the effect of Compound I in experimental stroke models.
Figure 6:
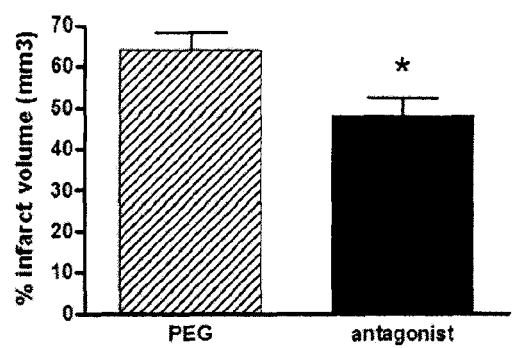

Compound I reduced infarct size in ischemia models. The effect of compound I in experimental stroke models was tested. When delivered 30 minutes pre-ischemia (i.p. injection), compound I at 50 mg/kg significantly reduced infarct volume, compared to vehicle PEG400 (polyethylene glycol 400). FIG. 6A shows the comparison between PKRA439 (antag) and control (PEG) at different levels of the brain (from rostral to caudal, 1-6). Compound I-treated rats had smaller infarct at almost every level. FIG. 6B shows a significant difference between compound I and PEG (control) groups (*$p<0.05$, n=5) in infarct volume.

Example VI

Methods for Seizure Assessment, Seizure Induction, the Seizure Model and Quantitation Adult male mice, C57BL/6 (from Charles River) or PK2 knockout and wild-type littermate (mix background C57BL6 and CD1) mice, weighing 20-30 g, were housed in groups, separated by sex, under normal 12 hour light/dark cycle With water and food at libitum. PK2 (−/−) mice were generated as described by (Li et al, in progress) and were produced by crossing PK2 (+/−) mice and verified with southern blot. Briefly, the PK2 gene was disrupted in embryonic stem cells by homologous recombination using a targeting vector in which exon 1 and 2 were replaced with a luciferase reporter gene and a neomycin-resistance cassette upstream of the PK2 promoter.

All seizure activity was assessed by placing individual mice in a single plexi-glass cage, with open tops or cage tops to prevent animals from jumping out of the cage. Animals were then assessed for seizure activity based on a modify Racine scale: Stages 1-2: immobility and forelimb extension with rigid posture; head bopping; tail stiffening; stage 3: low intensity and transient unilateral forelimb myoclonus, defined as rhythmical shaking in forelimb lasting for about 3-30 secs; stage 4; bilateral forelimb myoclonus with rearing; stage 5 (S5): whole body clonic-tonic with loss of posture and spontaneous jumping (popcorn effect). For some pilocarpine experiments, animals were also co-monitored with electroencephalography (EEG). The onset time of S5 was recorded by observing high amplitude and continuous spikes with co-observation of behavior indicative of S5 seizure.

All injections were administered through intraperitoneal injections (i.p.) Pilocarpine: to reduce muscarinic peripheral effects, all animals injected with pilocarpine were given 2 mg/kg of methylscopolamine (dissolved in saline 0.4 mg/ml) 30 minutes prior to injection. Pilocarpine-induced seizure was then initiated by injecting littermate mice (C57BL-6 or mix C57BL-6 with CD1) i.p. with (200 or 400 mg/kg) pilocarpine, respectively. Thereafter, animals were then assessed for seizure, as describe above, and sacrificed according to the following time course (30, 1 hr, 3 hrs, 6 hrs, 12 hrs, 36 hrs, 72 hrs). For groups within the pentylenetetrazol (metrazol, PTZ), mice were administered 75 mg/kg PTZ and subsequently monitored for 20 minutes. PTZ kindling were accomplished by administering 45 mg/kg PTZ every other day for 14 days. Animals that reach S5 on the first day were not included in the experiments. Each animal was injected and monitored for S5 seizure. Once S5 is reached, the animal was considered kindled, and was taken out of the injection regimen.

All mice undergoing surgery were anesthetized with Ketamine (100 mg/kg, i.p.) and Xylazine (5 mg/kg, i.p.). Mice anesthetize condition were assessed by toe pinch reflex. Animals were monitored continuously during surgery and supplemental anesthesia (Ketamine 25 mg/kg and Xylazine 1.25 mg/kg) were given if necessary. Electroencephalography (EEG) implantation was conducted according to Chemelli et al. Briefly, mice were deeply anesthetized with ketamine/xyalazine mixture, and standard surgical and stereotaxic procedures were used for electrode implantations into cranium bilaterally at (AP 1.1, ML+/−1.45 and AP −3.5, ML+/−1.45). Additionally two EMG electrodes were also anchored to the nuchal muscaulature. Following insertion, holes were secured by cementing the implants to the skull with dental acrylic. Mice were then housed separately, immediately after recovery. For ICV injection, mice were anesthetized and using standard stereotaxic procedures, a stainless steel cannula was inserted into the left ventricle. On the day of experiment, mice were briefly anesthetized with isoflourane. A plastic tube and adapter were then connected to the cannula, and animals were subsequently injected with either synthetic PK2 dissolved in aCSF (1 µg or 4 µg), or aCSF. Animals were then allow to rest for 30 mins, follow by injection of methylscopolamine (2 mg/kg), wait 30 mins and seizure was then subsequently induced with pilocarpine (400 mg/kg).

In situ hybridization was done according to Cheng et al 2001. Antisense and sense riboprobes containing the 3' UTR of mouse PK2 (GenBank accession number AF487279; residues 1147-2211), PKR1 (3' UTR) and PKR2 (3' UTR) were generated. Animals were killed at their respected time point and brains were quickly removed and frozen in −20 degrees Celsius isopentane, and stored at −70 degrees Celsius until use. Sections were then cut at 20-µm and processed for in situ as described by Winzer-Serhan et al. mRNA distributions from autoradiograms and emulsion-dipped sections were then analyzed and quantified with a system called MCID (Imaging Research). Calibration curve was generated by optical density versus radioactivity (disintegrations per minute (d.p.m.) per mg tissue wet weight) using 14 C standards. All data were normalized with respect to background.

Example VII

Pilocarpine-Induced Seizure Activates PK2 and PKR2 MRNA Expression

Figure 7:
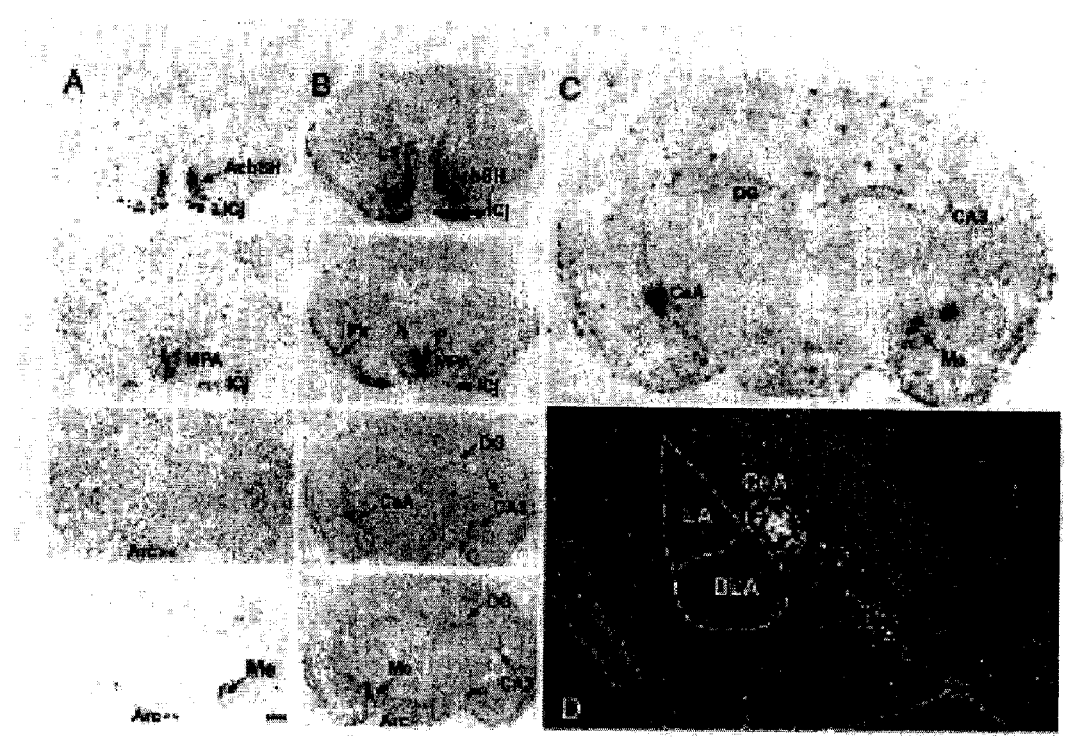
FIG. 7 is a series of images showing mRNA expression of PK2 and PKR2.
Figure 8:
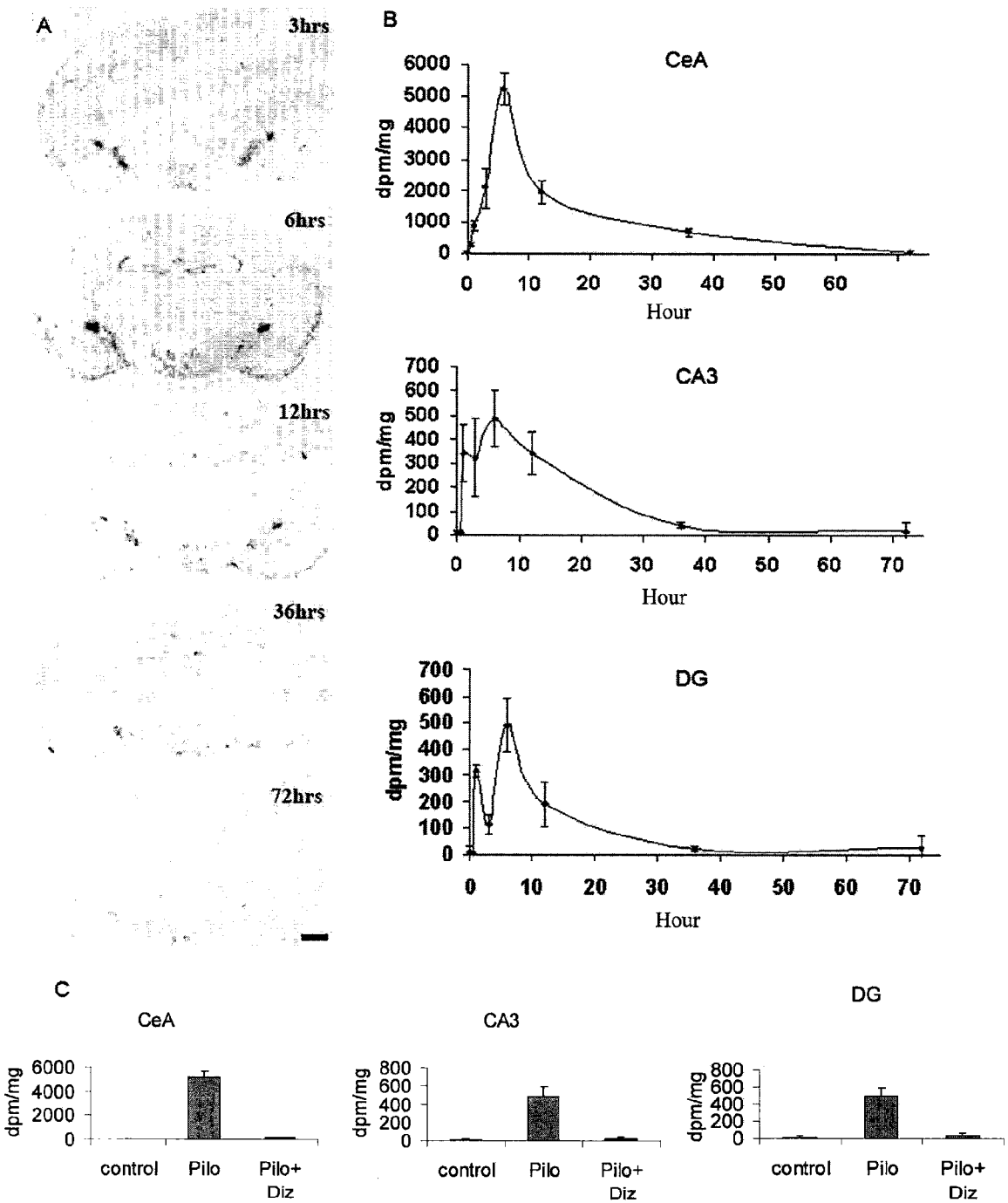
FIG. 8 shows a series of images and graphical representations depicting a time course of PK2 mRNA induction in CeA, CA3 and dentate gyrus, after treatment with pilocarpine: from 0 hrs-72 hrs. Pilocarpine induced a fast, temporal induction of PK2, which peaks at 6 hours.
Figure 9:
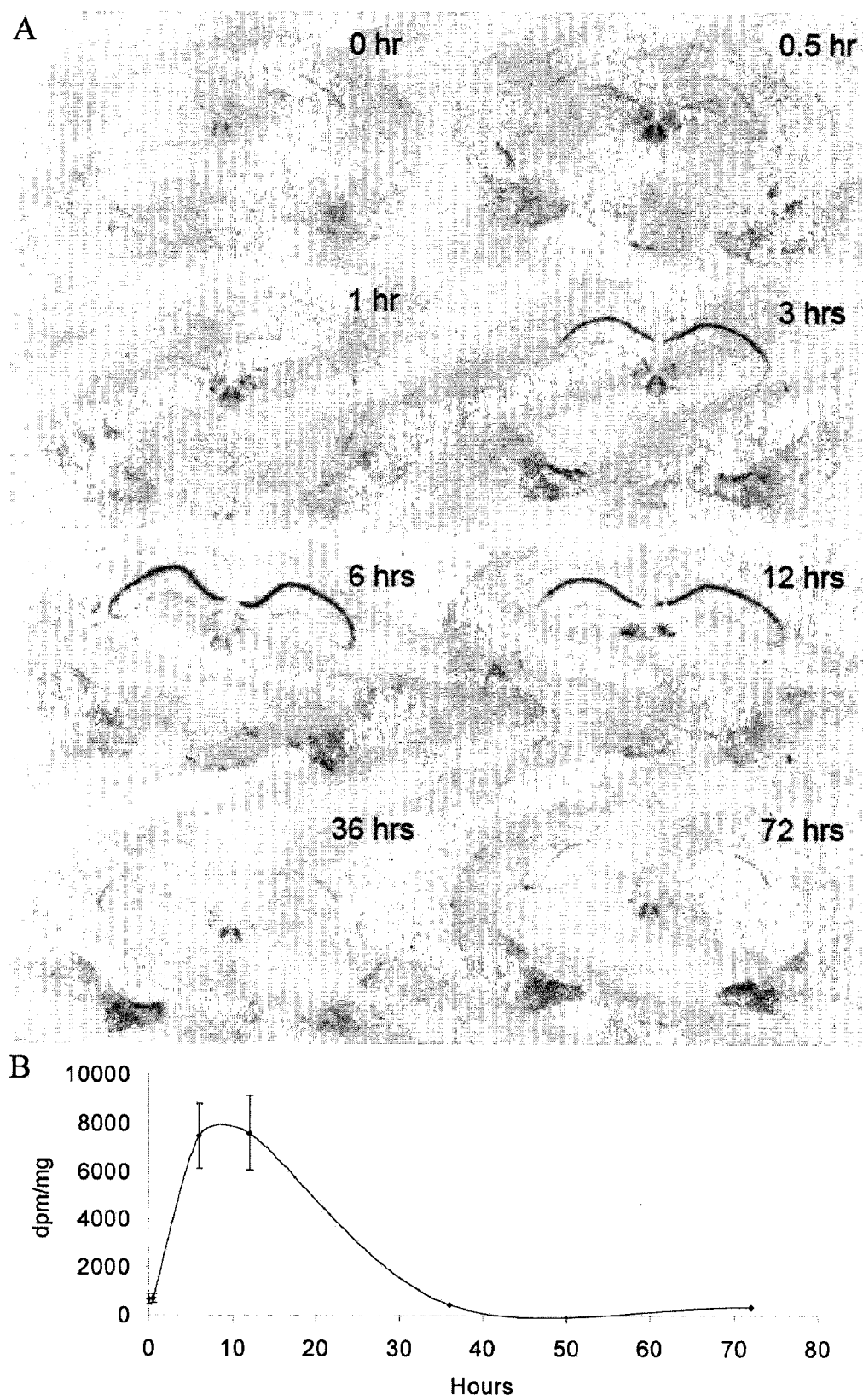
FIG. 9 shows a series of images and graphical representations depicting a time course of PKR2 mRNA upregulation within the CA1 and CA2 of the hippocampus. Pilocarpine quickly and dramatically upregulates PKR2 in the hippocampus, peaking at 6-12 hours.
Figure 10:
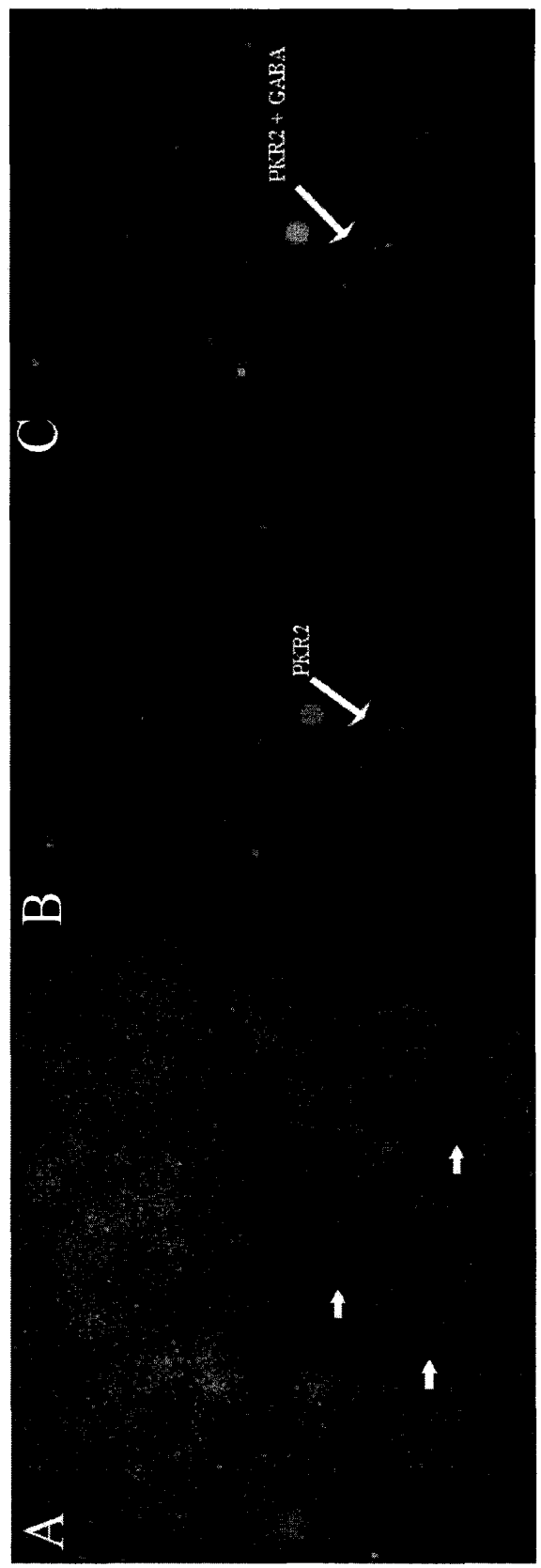
FIG. 10 shows a series of dark field photographic images.
Figure 11:
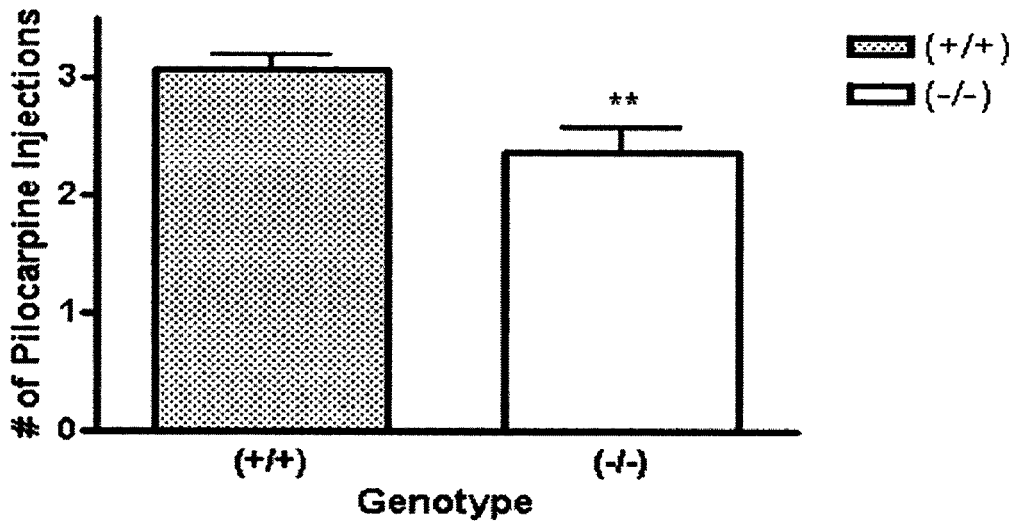
FIG. 11 is a series of graphical representations.
Figure 11:
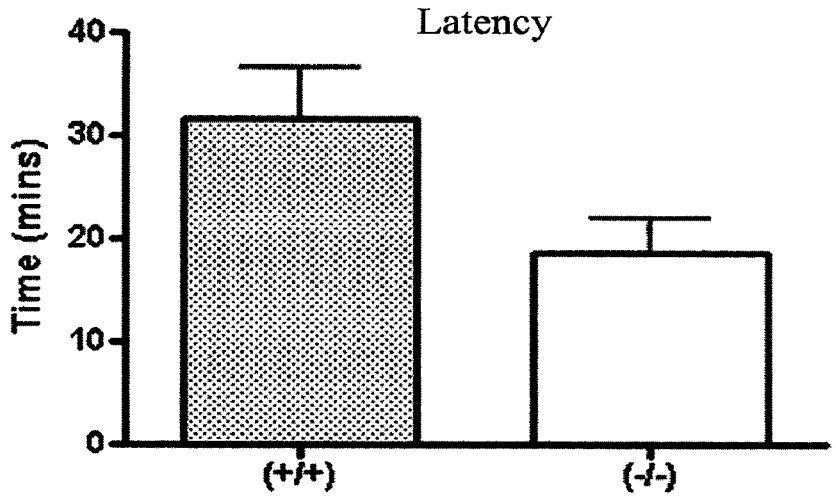
Figure 11:
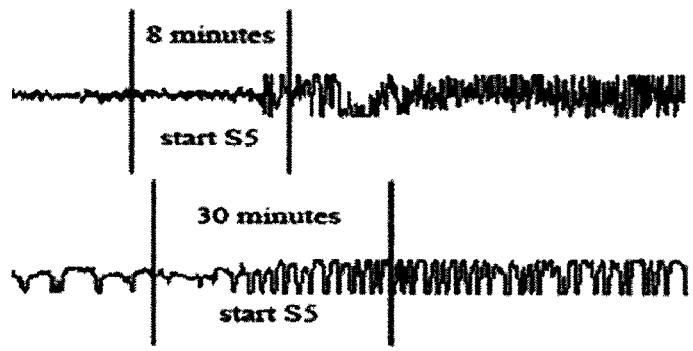

PK2 mRNA in response to pilocarpine induced-seizure was investigated. Seizure observations were conducted according to a modified Racine Scale. Only mice that reached at least stage 3 were used for subsequent analysis. As shown in FIG. 7, PK2 mRNA expression was dramatically induced and/or upregulated in several brain regions of adult mice after pilocarpine-induced-seizure. PK2 mRNA was induced in a number of areas such as the lateral septum (LS), bed nucleus of stria terminalis (BST), dentate gyrus (DG), CA3 of hippocampus (CA3), the central nucleus of amygdala (CeA), piriform cortex (Pir), and paraventricular hypothalamic nucleus (PVN). In addition, ectopic expression of PK2 was observed throughout the cortex and some PK2 expression within the hilus of the hippocampus. PK2 mRNA was also upregulated in several brain regions, including the shell of nucleus accumbens (AcbSH), medial preoptic area (MPA), islands of Calleja (ICj) and medial amygdala (Me).

Example VIII

PK2 and PKR2 MRNA induction follows a temporal time course and does not Colocalized with CRH A time course analysis for PK2 mRNA induction and upregulation in the pilocarpine-induced seizure model was performed. A total of seven time points (30 minutes, 1 hr, 3 hrs, 6 hrs, 12 hrs, 36 hrs, and 72 hrs post pilocarpine injection) were analyzed. Quantitative analysis indicated that PK2 mRNA induction within the amygdala (CeA) started 30 minutes after injection of pilocarpine or approximately 15 minutes after initial Stage 1-2 seizure (FIGS. 2A-B). PK2 induction gradually increased with respect to time after pilocarpine injection, peaking at 6 hours, and gradually decreased to basal level by 72 hours (FIGS. 2A-B). At its peak levels, PK2 mRNA was induced by over 100-fold over in CeA. A similar temporal profile was also observed in CA3 and dentate gyrus (FIG. 3B), although the amplitude of induction was much smaller than the CeA.

Interestingly PKR2 mRNA was highly induced (FIG. 3) within the CA1/CA2 area of the hippocampus. PKR2 followed a similar temporal induction profile with a peak level around 6-12 hours. It is known that pyramidal cells within the DG send long axonal projections that wraps around the CA3 and terminating at the CA1/CA2. It is thus interesting to observe that PK2 mRNA is induced in the DG and CA3 while its receptor (PKR2) is induced at the site of termination. It should be noted the upregulation of PK2 to pilocarpine-induced seizure is fast. PK2 induction within the CeA could be observed as early as 30 minutes after initial injection of pilocarpine, and since it takes approximately 10-15 minutes for the first sign of seizure to occur, the induction of PK2 can occur approximately 15 minutes after the initial seizure. Since CRH is a known molecule important in epilepsy and is abundantly within the amygdala, PK2 may also be part of the CRH pathway. Interestingly, double-labeling of 35S-PK2 and dig-CRH within CeA indicated that pilocarpine-induced PK2 expression in the central amygdala does not colocalize with CRH (FIG. 4A), suggesting a separate and perhaps novel pathway.

Example IX

PK2 Induction is Pilocarpine-Seizure-Dependent

To demonstrate that the PK2 induction/upregulation is seizure-dependent, diazepam (a $GABA_A$ agonist and an anti-convulsant) was delivered prior to pilocarpine injection to abolish seizure activity. In situ hybridization analysis indicated that PK2 mRNA induction/upregulation in the brain regions, including the CeA (FIG. 3D), CA3 and dentate gyrus were completely abolished in animals pretreated with diazepam. This suggests that the induction and/or upregulation of PK2 in these areas are due to the seizure activity provoked by pilocarpine and not other non-specific effects of the drug.

It has been previously reported that some mice strain responds to the presence of LiCl without pilocarpine administration, and that LiCl alone could contribute to similar but different outcome in pathology. To address this, PK2 mRNA induction with different strains of mice (CD1/C57Bl6 hybrids, CD1 inbred) using pilocarpine-induced convulsant with and without LiCl was examined. All of these conditions yielded successful induction of PK2 mRNA (data not shown), indicating that PK2 mRNA induction is specifically induced by pilocarpine-induced seizure.

PK2 induction was further examined with Pentylenetetrazol (PTZ, Metrazol), a known GABA antagonist. In the PTZ seizure model, only a modest upregulation of PK2 mRNA at the medial nucleus of the amygdale was observed (data not shown). No induction of PK2 mRNA in any other brain areas was apparent, suggesting that the induction of PK2 mRNA is specific to pilocarpine induced-seizure. This is of particular interest since pilocarpine is most often used as a model for temporal lobe epilepsy. Administration of pilocarpine in animals will induce status-epilepticus (continuous S3-S4 seizure), followed by neuromorphological changes similar to human temporal lobe epilepsy patients during a phase known as the quiet period, and finally the appearance of spontaneous seizure. PTZ may also be acting differently in terms of onset of action. That is, it may be very quick and short acting, and PK2 induction cannot be captured during that short time.

Example X

PK2−/− Mice Exhibit Increased Sensitivity to Repeated Sub-Threshold Pilocarpine-Induced Seizure The fast induction and/or upregulation of PK2 mRNA by pilocarpine-induced seizure suggest that PK2 may be involved in the process of seizure onset. To study this, the seizure threshold in PK2-deficient mice was investigated. Mice deficient in the PK2 gene (N=11) were compared to littermate wild type (WT, N=15) controls with repeated sub threshold doses of pilocarpine. For this study, a sub-threshold dose of pilocarpine (200 mg/kg) was defined as a dose that does not induce S5 seizure in normal WT mice. Pilocarpine was injected every 30 minutes until a S5 convulsion was observed. Although there were no differences in acquisition of stage 1-3, PK2−/− mice reached S5 seizure with significantly lower doses of pilocarpine (FIG. 5A, unpaired student t-test p<0.05). These studies indicate that PK2−/− mice have reduced seizure induction threshold by pilocarpine Example XI PK2−/− Mice are More Sensitive to Single Injection of Convulsive Pilocarpine Dose
A single high dose of pilocarpine (400 mg/kg) induced S5 seizure was carried out. For this study, 13 animals were used per group. Animals were injected with a single dose of pilocarpine and the time of S5 seizure acquisition was measured. All animals had at least one episode of S5 seizure, except for one WT. Progressions of S1-S3 seizures were relatively similar between the three groups, however PK2−/− mice took significantly shorter time to reach S5 (FIG. 5B) (student t-test p<0.05). A subset of the 13 animals within each group (5/13) was implanted with electrodes to measure EEG signals. Behaviorally, both EEG groups, WT and PK2−/−, displayed shorter latency time for seizure induction with pilocarpine, but PK2−/− mice still had a shorter latency time. For EEG recordings, the onset of the S5 seizure was quantified from EEG, as observed with fast and continuous and simultaneously behavioral monitoring, which agreed perfectly with simultaneously behavioral observations.

Example XII

Figure 12:
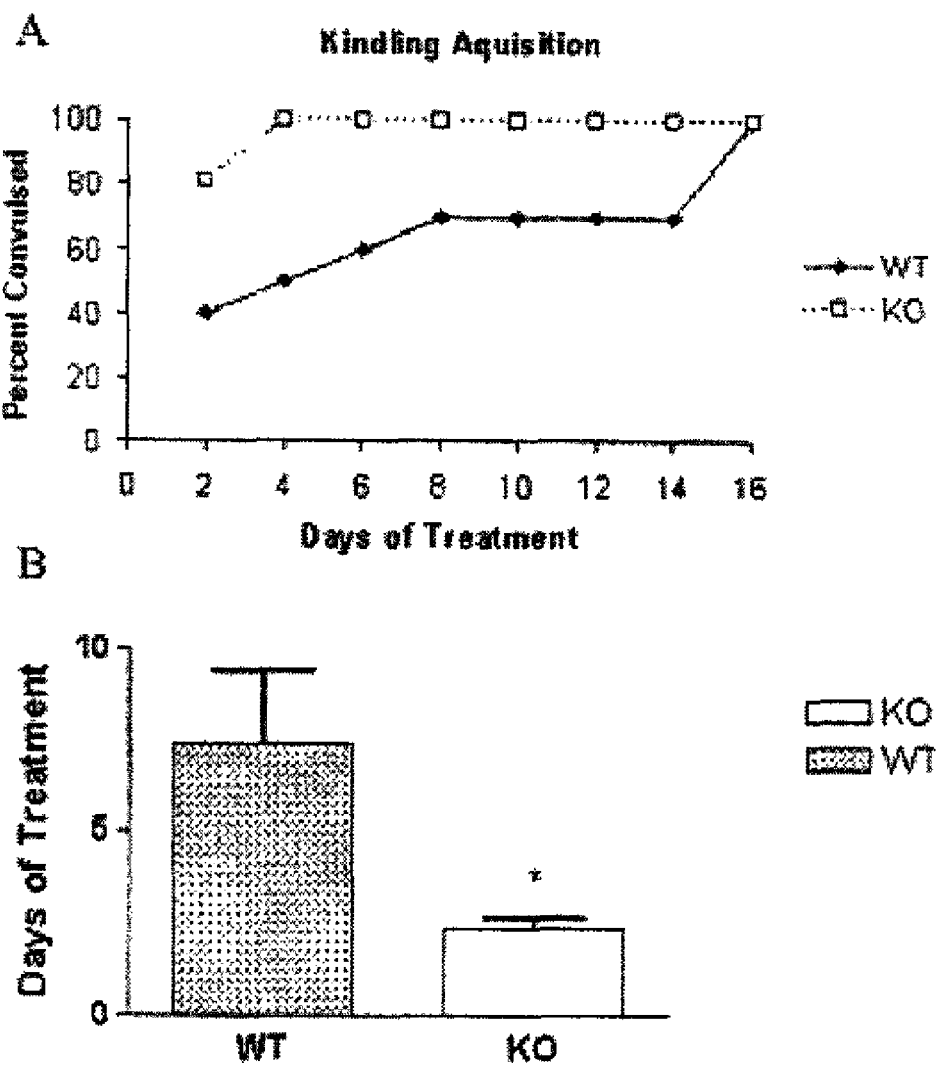
FIG. 12 is a series of graphical representations showing Kindling acquisition over the course of repeated treatment of PTZ (45 mg/kg) on days 2-16 (every other day).

Increased Sensitivity of PK2−/− Mice to Kindling by Sub-Threshold Doses of Pentylenetetrazole (PTZ)
The robust PK2 induction and/or upregulation after pilocarpine-induced seizure suggested a possibility of its role in epileptogenesis. Hence, a PTZ kindling model, an established epileptic (kindling) model for mice, was used to investigate the role of PK2 on epileptogenesis. PTZ kindling was accomplished by administering PTZ (45 mg/kg IP) every other day for 2 consecutive weeks. Animals that reach S5 on the first day were not included in the experiments. Each animal was monitored for 45 minutes every day for the incidence and onset of convulsions. The maximum response was recorded for each animal. Mice were considered fully kindled when exhibiting stage 5 seizures with the same sub threshold dose of previous day(s). Once S5 seizure is reached, the animal was considered kindled, and was taken out of the injection regimen. As shown in FIG. 12, 80% of PK2−/− mice achieve kindled state on the 2nd day, while it took 14 days for WT animals to achieve only 70% of kindled animals. Overall PK2−/− mice took significantly less time for kindling acquisition (p<0.05 unpaired student t-test), suggesting that PK2 may play a role in epileptogenesis.

Example XIII

PKR2 MRNA in the amygdala is colocalized with GABA
PK2 has been previously shown to increase action potential of neurons, suggesting that PK2 in this case could excite interneurons within the amygdala. A colocalization experiment to examine whether PKR2 colocalize with GABA was performed. Immunohistochemistry studies showed that PKR2 mRNA is colocalized with GAD-containing interneurons in the amygdala. Qualitative analysis indicated that approximately 80% of all PKR2 mRNA in the amygdala were colocalized with the GABA. This suggests that PK2 may modulate excitation though interaction with the GABAergic system (FIG. 4). An additional colocalization study with PKR2 and the $GABA_A$ receptor also revealed the presence of colocalization of PKR2 with the $GABA_A$ receptor.

Example XIV

PK2 inactivates $\alpha\beta\gamma$ $GABA_A$ currents

Figure 13:
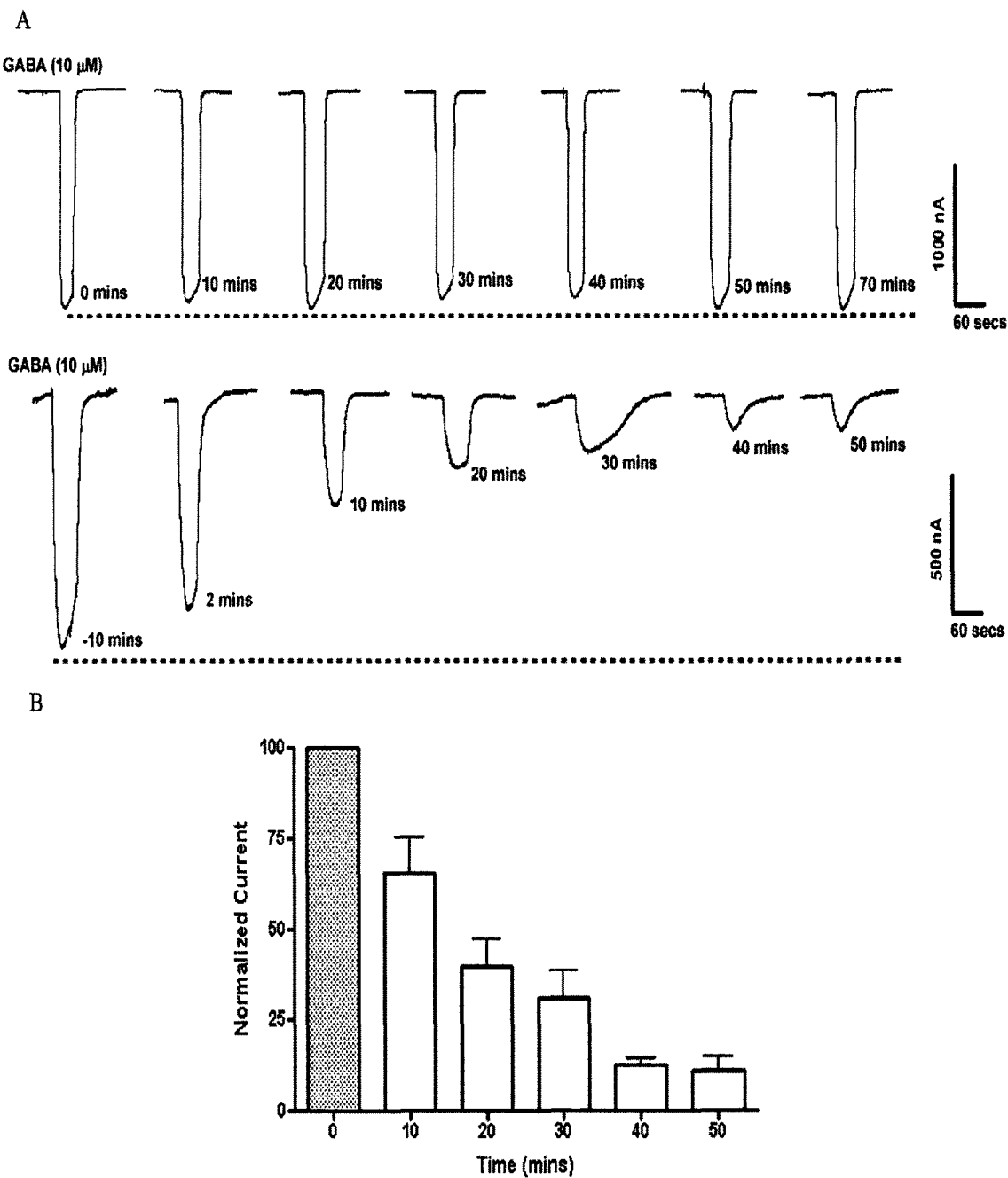
FIG. 13 is a series of graphical representations showing PK2-induced reduction of GABA ($\alpha 1\beta 1\gamma 2$) currents.

Multiple studies have found a complex system of inhibition, disinhibition, and various physiological consequences, depending on the circuitry and subtypes involved; all of which have important consequences in epileptogenesis. The role of PK2 and $GABA_A$ receptor, especially with the $\alpha\beta\gamma$-$GABA_A$ which are found in the amygdale was investigated. Some of the following sounds like in methods again. To do this study, a mixture of RNA containing $\alpha1\beta1\gamma2S$ with or without PKR2 was injected into Xenopus oocytes. GABA currents were then measured using the two-electrode voltage clamp with a holding potential of −70 mV, 4-6 days post injection. Repeated exposure (every 10 mins) with GABA (10 µM) to Xenopus oocytes ($\alpha\beta\gamma$-$GABA_A$ or $\alpha\beta\gamma_7$-$GABA_A$+ PKR2 containing) induced a reproducible and stable current over a long-term recording (>1 hr). As depicted in FIG. 13, PK2 induces a steady and fast inhibition of GABA-evoked currents of a maximum of 75% of normalized baseline. This data suggest that activation of the PK2 receptor, especially after seizure where both PK2 and PKR2 are highly upregulated, may cause a severe attenuation of GABA currents in certain regions of the brain and thus modulates the excitation/inhibition after seizure.

The above examples show that PK2 is an important regulator of seizure onset and epilepsy. PK2 mRNA is dramatically up-regulated in pilocarpine-induced seizures, in regions that are critical for seizure induction, including amygdala, hippocampus and cortices. PK2-deficient mice display an increased sensitivity to pilocarpine induced-seizures and exhibit increased rate for kindling acquisition. Previous studies have demonstrated that PK2 increases depolarization and action potential in neurons, possibly by modulating inwardly rectifying K+ channels. PK2 also enhances the excitability of PKR2-positive PVN neurons (Yuill et al.). Thus, PK2 signal is likely to increase the excitability of neurons that express PKR2. The majority of the PKR2 was colocalized with GABA in the interneurons of the amygdala. Numerous studies have shown that the amygdala is a critical routing center for seizure propagation, due in part to its multisynaptic inputs and ability to propagate excitatory signal throughout the brain quickly. It is also known that the amygdala has the lowest threshold for electrical kindling. Thus, the present invention suggests that PK2 may modulate seizure by increasing firing rate of interneurons within the amygdala. The ability to modulate K+ channel may also be important and the ion channel itself is especially critical for seizure propagation due in part to its ability to stabilize cellular membrane. Mutations and/or modulations of a number of K+ channels can lead to epilepsy in mice and humans. A-type K+ channels, for example, are decreased within the hippocampus in a pilocarpine model which may attribute to an increase in dendritic excitability in CA1 pyramidal neurons. An exciting prospect of this is that an increase in neuronal network excitation is established without the need for new synaptic formations.

Figure 2:
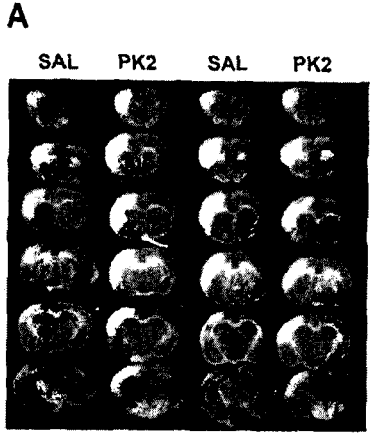
FIG. 2A are images showing post-ischemic increases in brain infarct size and volume after ICV delivery of PK2.
FIG. 2B is a graphical representation showing post-ischemic quantitation of brain infarct size and volume after ICV delivery of PK2.
FIG. 2C is a graphical representation of the data presented in FIG. 2B plotted as a mean result from all six levels of infarct.
FIG. 2D is a graphical representation showing the dose dependent effect of PK2 on increasing average infarct volume.
Figure 2:
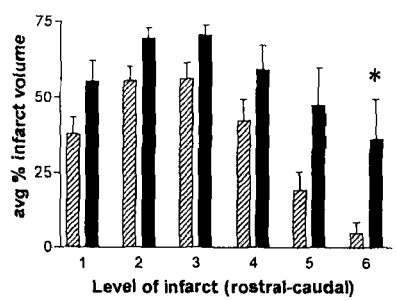
Figure 2:
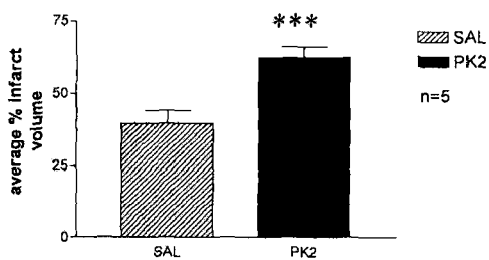
Figure 2:
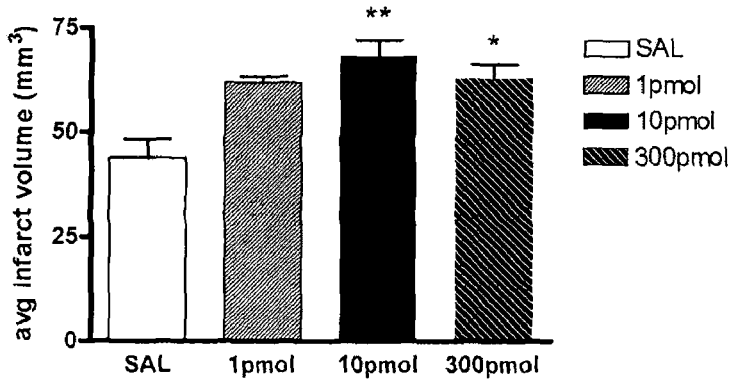
Figure 3:
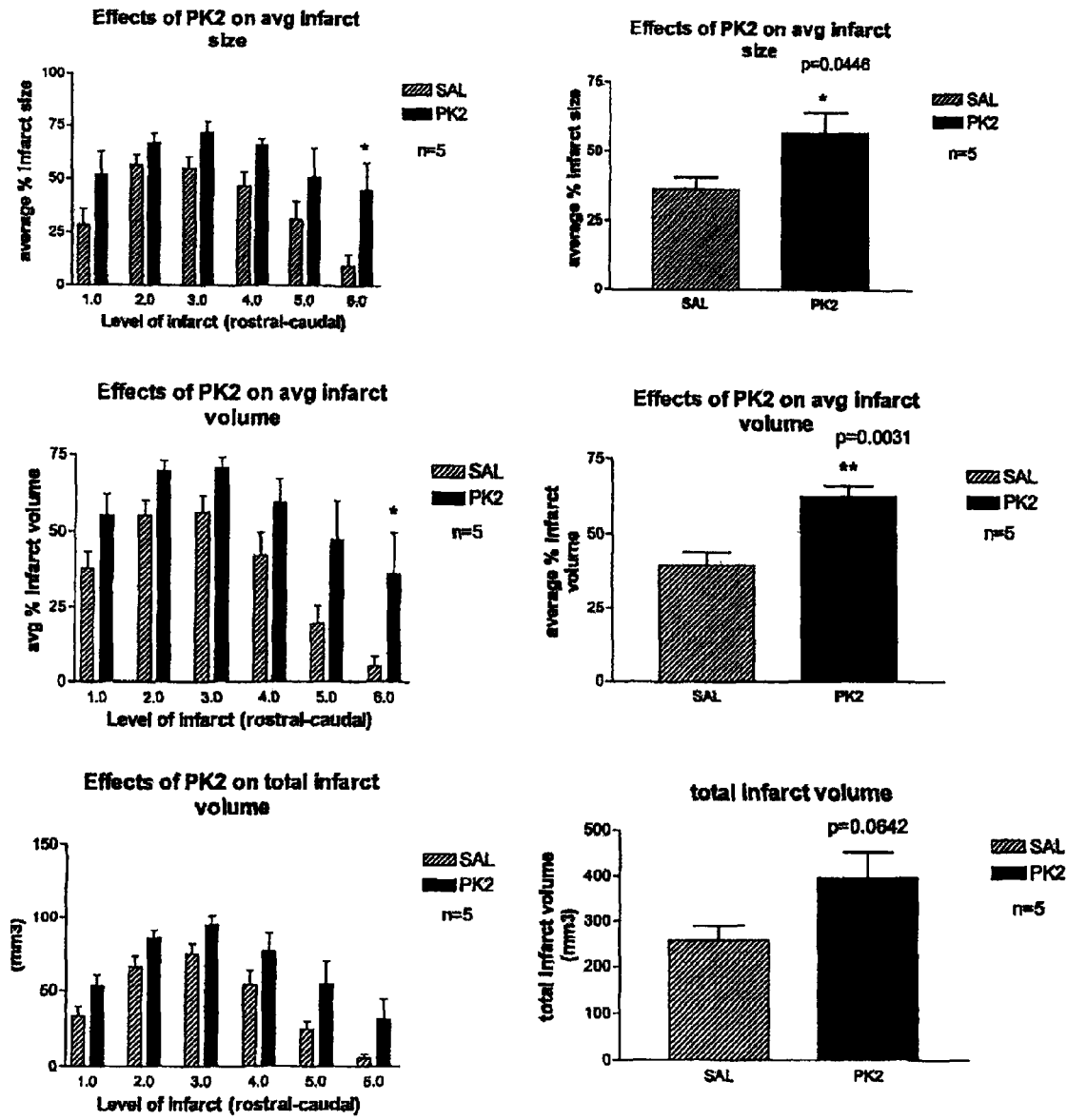
FIG. 3 are a series of graphs showing post-ischemic quantitation of brain infarct size and volume after ICV delivery of PK2.

In addition to seizure modulation, PK2 may also play a role in the development of epilepsy. The present invention describes that the administration of pilocarpine in animals often leads to status-epilepticus (SE, continuous S3-S4 seizure), followed by a major induction of PK2 and PKR2 mRNA in regions that are thought to be important to epileptogenesis. Pilocarpine is an epileptic model which induces very similar morphological alterations seen in human patients. It is thought that alterations such as cell loss, gliosis, and axonal sprouting may all play a role in epileptogenesis. Others have also demonstrated neurogenesis occurring within the amygdala and newly formed ectopic granule-like cells within the hilus and molecular layer of the dentate-gyrus. The neurogenic effect of PK2, including the differentiation and migration on neural progenitors, may contribute to the overall pathology of pilocarpine induced epilepsy. In addition, it has been suggested that genes that respond quickly to hyperneuronal excitation, as a result of convulsion, may play an important role in long-termed neuroplasticity. Time course analysis indicated that the increase in mRNA was very fast but temporal—for example, PK2 induction within the CeA of the amygdala was observed within 15 minutes. This rate of induction is similar to immediately early genes (IEG) such as c-fos. Similar to c-fos and other IEGs, PK2 mRNA also contains several instability repeats of AUUUA in its 3' unstranslated region that may underlie very short half time of PK2 mRNA. In addition the peak of both PK2 and PKR2 expression in the CeA and CA1/CA2, respectively (6 hr post pilocarpine injection) is over 100-fold over its basal level for PK2 and about 7-fold for PKR2 (FIGS. 2 and 3). This degree of mRNA upregulation is much higher than previous gene upregulation in any seizure models. In the kindling model, 264 genes have been reportedly upregulated, with the most strongly regulated one being homer 1A, which is upregulated about 5-6 fold in both hippocampus and amygdala. This high degree of upregulation may demonstrates an important role of PK2 in seizure induction. Thereafter, PK2 increases with respect to time, peaking at 6 hours and returning to basal after 72 hours. Induction intensity varied within different regions, with the highest induction for PK2 within the CeA of the amygdala and CA1/CA2 for PKR2. Blocking of seizure activity with Diazepam eliminated induction of both PK2 and PKR2, suggesting that PK2 induction is dependent on seizure, and not a result of an unspecific activity of pilocarpine.

PTZ kindling experiments indicated that PK2-deficient mice required a significantly less time to reach kindling state—this in addition to its expression profile after SE, suggests that PK2 plays a role in epileptogenesis. Although electrical kindling is most often used, chemical kindling is also an effective and acknowledged kindling model. In particular, Pentylenetetrazole (PTZ; metrazol), a GABA receptor antagonist, has been used to effectively produce kindled state in both rat and mice. Similar to electrical kindling, the response is proportional to the intensity of the stimulus and can be elicited even after 2-4 weeks of withdrawal from treatment. An added benefit for the PTZ model is that it does not involve an invasive surgical procedure which can damage and/or confound the experiment. Using a two-electrode voltage-clamp system with $X.$ $laevis$ oocytes, PKR2 activation leads to a robust attenuation of $GABA_A$ currents was demonstrated. This effect is counter-intuitive, as kindling experiments in PK2-deficient mice suggest that PK2 may serve as a halting mechanism for seizure propagation. Yet activation of PKR2 seems to attenuate, instead of augmenting GABA signals. A number of reasons may explain this paradoxical attenuation effect of PK2 signaling on GABA currents. GABAergic system is a complex network with various physiological consequences which will vary across different brain regions, depending on, connectivity, state of brain, and class types. There are now accumulating data suggesting that GABAergic neurotransmission can be excitatory in both normal and pathological conditions. Also, one function of the GABAergic system is to help synchronize and generate oscillation, suggesting that a decrease in GABA maybe protective for seizure activity. If PK2 signals impinge on these excitatory or synchronization GABA neurotransmission, the attenuation of GABA currents may link to the seizure-suppression effect of PK2. The experiments have demonstrated that PK2 acts to suppress seizure onset during pilocarpine-induced convulsion and plays a role in suppressing epileptogenesis.

Although the invention has been described with reference to the above example, it will be understood that modifications and variations are encompassed within the spirit and scope of the invention. Accordingly, the invention is limited only by the following claims.

What is claimed is:

1. A method for treating a cerebrovascular disease in a subject comprising administering to the subject a PKR2 receptor antagonist, thereby treating cerebrovascular disease, wherein the cerebrovascular disease is cerebral ischemia and infarct size is reduced as compared to infarct size without administration of the antagonist, and wherein further the PKR2 receptor antagonist is a morpholine carboxamide derivative having the following structure:

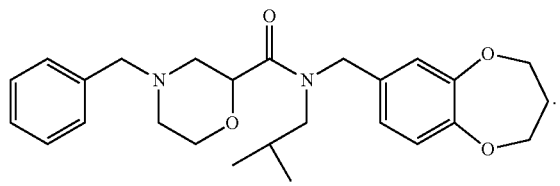

2. The method of claim 1, wherein the compound is administered parenterally.

3. The method of claim 2, wherein the compound is administered by intraperitoneal injection.

4. The method of claim 1, wherein the PKR2 receptor antagonist is administered before, during or after cerebral ischemia.

5. The method of claim 1, wherein the subject is a mammal.

6. The method of claim 5, wherein the mammal is a human.

* * * * *

UNITED STATES PATENT AND TRADEMARK OFFICE
CERTIFICATE OF CORRECTION

PATENT NO. : 8,101,158 B1
APPLICATION NO. : 12/025673
DATED : January 24, 2012
INVENTOR(S) : Zhou et al.

Page 1 of 1

It is certified that error appears in the above-identified patent and that said Letters Patent is hereby corrected as shown below:

Please amend the paragraph beginning on Line 17 of Column 1 and ending on Line 19 of Column 1 as follows:

--This invention was made with government support under grants MH067753 and NS037520 awarded by the National Institutes of Health. The government has certain rights in the invention.--

Signed and Sealed this
Tenth Day of April, 2012

David J. Kappos
*Director of the United States Patent and Trademark Office*